US012716887B2

(12) United States Patent
Sarkisian et al.

(10) Patent No.: US 12,716,887 B2
(45) Date of Patent: Aug. 25, 2026

(54) METHODS OF REDUCING CILIOGENESIS WITH ALTERNATING ELECTRIC FIELDS

(71) Applicant: Novocure GmbH, Root (CH)

(72) Inventors: Matthew R. Sarkisian, Gainesville, FL (US); Lilach Avigdor, Haifa (IL); Preshita Desai, Pomona, CA (US)

(73) Assignee: Novocure GmbH, Baar (CH)

(*) Notice: Subject to any disclaimer, the term of this patent is extended or adjusted under 35 U.S.C. 154(b) by 815 days.

(21) Appl. No.: 18/070,957

(22) Filed: Nov. 29, 2022

(65) Prior Publication Data

US 2023/0168242 A1 Jun. 1, 2023

Related U.S. Application Data

(60) Provisional application No. 63/283,740, filed on Nov. 29, 2021.

(51) Int. Cl.

| | |
|---|---|
| ***G01N 33/50*** | (2006.01) |
| ***A61N 1/32*** | (2006.01) |
| ***C12N 13/00*** | (2006.01) |

(52) U.S. Cl.

CPC .......... *G01N 33/5005* (2013.01); *A61N 1/32* (2013.01); *C12N 13/00* (2013.01)

(58) Field of Classification Search

CPC ...... A61N 1/32; A61N 1/36002; C12N 13/00; G01N 33/5005

See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |

(Continued)

FOREIGN PATENT DOCUMENTS

| | | |
|---|---|---|
| CA | 2999576 A1 | 9/2019 |
| WO | 2021136960 A1 | 7/2021 |

OTHER PUBLICATIONS

Stupp et al., "Effect of Tumor-Treating Fields Plus Maintenance Temozolomide vs. Maintenance Temozolomide Alone on Survival in Patients with Glioblastoma: A Randomized Clinical Trial," JAMA, vol. 318, pp. 2306-2316, 2017.

(Continued)

*Primary Examiner* — Jennifer Wecker

(74) *Attorney, Agent, or Firm* — Potomac Law Group, PLLC

(57) ABSTRACT

A method of determining susceptibility of cancer cells to treatment with alternating electric fields, or of reducing the viability of cancer cells by applying alternating electric fields, by measuring percentage of ciliated cancer cells or by measuring average length of a primary cilia of cancer cells. A method of treating Huntington's disease by applying alternating electric fields to a brain of a subject.

19 Claims, 17 Drawing Sheets

(56) References Cited

U.S. PATENT DOCUMENTS 7,715,921 B2 5/2010 Palti
7,805,201 B2 9/2010 Palti
7,890,183 B2 2/2011 Palti et al.
7,912,540 B2 3/2011 Palti
7,917,227 B2 3/2011 Palti
8,019,414 B2 9/2011 Palti
8,027,738 B2 9/2011 Palti
8,170,684 B2 5/2012 Palti
8,175,698 B2 5/2012 Palti et al.
8,229,555 B2 7/2012 Palti
RE43,618 E 8/2012 Palti
8,244,345 B2 8/2012 Palti
8,406,870 B2 3/2013 Palti
8,447,395 B2 5/2013 Palti et al.
8,447,396 B2 5/2013 Palti et al.
8,465,533 B2 6/2013 Palti
8,706,261 B2 4/2014 Palti
8,715,203 B2 5/2014 Palti
8,718,756 B2 5/2014 Palti
8,764,675 B2 7/2014 Palti
9,023,090 B2 5/2015 Palti
9,023,091 B2 5/2015 Palti
9,039,674 B2 5/2015 Palti et al.
9,056,203 B2 6/2015 Palti et al.
9,440,068 B2 9/2016 Palti et al.
9,655,669 B2 5/2017 Palti et al.
9,750,934 B2 9/2017 Palti et al.
9,910,453 B2 3/2018 Wasserman et al.
10,188,851 B2 1/2019 Wenger et al.
10,441,776 B2 10/2019 Kirson et al.
10,779,875 B2 9/2020 Palti et al.
10,967,167 B2 4/2021 Hagemann et al.
11,191,956 B2 12/2021 Giladi et al.
2004/0176804 A1 9/2004 Palti
2006/0167499 A1 7/2006 Palti
2006/0276858 A1 12/2006 Palti
2007/0225766 A1 9/2007 Palti
2007/0239213 A1 10/2007 Palti
2009/0076366 A1 3/2009 Palti
2012/0029419 A1 2/2012 Palti
2012/0283726 A1 11/2012 Palti
2012/0289955 A1* 11/2012 Marc ........................ A61K 8/19 606/41
2014/0330268 A1 11/2014 Palti et al.
2017/0120041 A1 5/2017 Wenger et al.
2017/0215939 A1 8/2017 Palti et al.
2017/0281934 A1 10/2017 Giladi et al.
2018/0001075 A1 1/2018 Kirson et al.
2018/0008708 A1 1/2018 Giladi et al.
2018/0050200 A1 2/2018 Wasserman et al.
2018/0160933 A1 6/2018 Urman et al.
2018/0202991 A1 7/2018 Giladi et al.
2018/0280687 A1 10/2018 Carter et al.
2019/0117956 A1 4/2019 Wenger et al.
2019/0117963 A1 4/2019 Travers et al.
2019/0224474 A1 7/2019 Yang et al.
2019/0308016 A1 10/2019 Wenger et al.
2020/0001069 A1 1/2020 Kirson et al.
2020/0009376 A1 1/2020 Chang et al.
2020/0009377 A1 1/2020 Chang et al.
2020/0016067 A1 1/2020 Gotlib et al.
2020/0023179 A1 1/2020 Bomzon et al.
2020/0061360 A1 2/2020 Hagemann et al.
2020/0061361 A1 2/2020 Hagemann et al.
2020/0069937 A1 3/2020 Naveh et al.
2020/0078582 A1 3/2020 Alon et al.
2020/0108031 A1 4/2020 Borst et al.
2020/0114141 A1 4/2020 Bomzon et al.
2020/0114142 A1 4/2020 Bomzon et al.
2020/0121728 A1 4/2020 Wardak et al.
2020/0129761 A1 4/2020 Bomzon et al.
2020/0146586 A1 5/2020 Naveh et al.
2020/0155835 A1 5/2020 Wasserman et al.
2020/0171297 A1 6/2020 Kirson et al.
2020/0179512 A1 6/2020 Giladi et al.
2020/0219261 A1 7/2020 Shamir et al.
2020/0269037 A1 8/2020 Hagemann et al.
2020/0269041 A1 8/2020 Zeevi et al.
2020/0269042 A1 8/2020 Giladi et al.
2020/0368525 A1 11/2020 Maag et al.
2021/0031031 A1 2/2021 Wasserman et al.
2021/0038584 A1 2/2021 Voloshin-Sela
2021/0060334 A1 3/2021 Avraham et al.
2021/0069503 A1 3/2021 Tran et al.
2021/0138233 A1 5/2021 Deslauriers
2021/0162228 A1 6/2021 Urman et al.
2021/0187277 A1 6/2021 Wasserman et al.
2021/0196348 A1 7/2021 Wasserman
2021/0199640 A1 7/2021 Patel et al.
2021/0203250 A1 7/2021 Wasserman
2021/0268247 A1 9/2021 Story et al.
2021/0299440 A1 9/2021 Deslauriers et al.
2021/0308446 A1 10/2021 Alon et al.
2021/0330950 A1 10/2021 Hagemann et al.
2021/0346694 A1 11/2021 Wasserman et al.
2021/0379362 A1 12/2021 Smith et al.
2021/0408383 A1 12/2021 Kalra et al.
2022/0095997 A1 3/2022 Wasserman
2022/0096821 A1 3/2022 Kirson et al.
2022/0118249 A1 4/2022 Bomzon et al.
2022/0161028 A1 5/2022 Giladi et al.
2022/0193435 A1 6/2022 Wasserman et al.
2022/0267445 A1 8/2022 Tran et al.
2022/0280787 A1 9/2022 Bomzon et al.
2022/0288395 A1 9/2022 Voloshin-Sela et al.
2022/0313992 A1 10/2022 Wasserman
2022/0323753 A1 10/2022 Voloshin-Sela et al.
2022/0387784 A1 12/2022 Kirson et al.
2022/0395699 A1 12/2022 Doyle
2022/0409893 A1 12/2022 Wasserman et al.
2023/0000384 A1 1/2023 Wasserman et al.
2023/0001197 A1 1/2023 Wasserman et al.
2023/0001221 A1 1/2023 Farber
2023/0009366 A1 1/2023 Voloshin-Sela et al.
2023/0019638 A1 1/2023 Wasserman

OTHER PUBLICATIONS

Stupp et al., “Maintenance Therapy With Tumor-Treating Fields Plus Temozolomide vs. Temozolomide Alone for Glioblastoma—A Randomized Clinical Trial,” JAMA, vol. 314, No. 23, pp. 2535-2543, Dec. 2015.

Stupp et al., “Radiotherapy plus Concomitant and Adjuvant Temozolomide for Glioblastoma,” The New England Journal of Medicine, vol. 352, pp. 987-996, Mar. 2005.

Stupp et al., “Effects of radiotherapy with concomitant and adjuvant temozolomide versus radiotherapy alone on survival in glioblastoma in a randomised phase III study: 5-year analysis of the EORTC-NCIC trial,” The Lancel Oncology, vol. 10, Issue 5, pp. 459-466, May 2009.

Tang et al., “Autophagy Promotes Primary Cillogenesis by Removing OFD1 from Centriolar Satellites,” Nature, vol. 502 (7470), pp. 254-257, Oct. 2013.

Voloshin-Sela et al., “Tumor-treating fields (TTFields) induce immunogenic cell death resulting in enhanced antitumor efficacy when combined with anti-PD-1 therapy,” Cancer Immunology, Immunotherapy, vol. 69, pp. 1191-1204, Mar. 2020.

Wang et al., “Reciprocal regulation of cilia and autophagy via the MTOR and proteasome pathways,” Autophagy, vol. 11, No. 4, pp. 607-616, Apr. 2015.

Wang et al., “The regulation of cilium assembly and disassembly in development and disease,” Development, vol. 145, No. 18, dev151407, Sep. 2018.

Wheway et al., “Signaling through the Primary Cilium,” Frontiers in Cell and Developmental Biology, vol. 6, Article 8, Feb. 2018.

Wurstle et al., “Temozolomide induces autophagy in primary and established glioblastoma cells in an EGFR independent manner,” Oncology Letters, vol. 14, pp. 322-328, Jul. 2017.

Yan et al., “Targeting autophagy to sensitive glioma to temozolomide treatment,” Journal of Experimental & Clinical Cancer Research, vol. 35, Article No. 23, Feb. 2016.

(56) References Cited

OTHER PUBLICATIONS

Yoshimura et al., "Signaling through the primary cilium affects glial cell survival under a stressed environment," Glia, vol. 59, Issue 2, pp. 333-344, Feb. 2011, Abstract.
Zhao et al., "A Transposon Screen Identifies Loss of Primary Cilia as a Mechanism of Resistance to SMO Inhibitors," Cancer Discovery, vol. 7, No. 12, pp. 1436-1449, Dec. 2017.
Akhshi et al., "A non-canonical Hedgehog pathway initiates ciliogenesis and autophagy," Journal of Cell Biology, vol. 220, No. 1, p. e202004179, Dec. 2020.
Arellano et al., "Development and distribution of neuronal cilla in mouse neocortex," J. Comp. Neurol., vol. 520, No. 4, pp. 848-873, Mar. 2012.
Berbari et al., "Hippocampal neurons possess primary cilla in culture," Journal of Neuroscience Research, vol. 85, Issue 5, pp. 1095-1100, Feb. 2007.
Bishop et al., "Type III adenylyl cyclase localizes to primary cilla throughout the adult mouse brain," The Journal of Comparative Neurology, vol. 505, Issue 5, pp. 562-571, Oct. 2007.
Cai et al., "Primary cilia are sensors of electrical field stimulation to induce osteogenesis of human adipose-derived stem cells," The FASEB Journal, vol. 31, No. 1, pp. 346-355, Oct. 2016.
Chang et al., "Tumor treating fields increases membrane permeability in glioblastoma cells," Cell Death Discovery, 4:113, 2018.
Chen et al., "Exposure to 16 Hz Pulsed Electromagnetic Fields Protect the Structural Integrity of Primary Cilla and Associated TGF-β Signaling in Osteoprogenitor Cells Harmed by Cigarette Smoke," Int. J. Mol. Sci., vol. 22, No. 13, p. 7036, Jun. 2021.
Das et al., "Apical abscission alters cell polarity and dismantles the primary cilium during neurogenesis," Science, vol. 343, No. 6167, pp. 200-204, Jan. 2014.
Deleyrolle et al., "Evidence for label-retaining tumour-initiating cells in human glioblastoma," Brain, vol. 134 (PT 5), pp. 1331-1343, May 2011.
Garcia et al., "How the Cillary Membrane Is Organized Inside-Out to Communicate Outside-In," Current Biology, vol. 28, No. 8, pp. R421-R434, Apr. 2018.
Garcia-Gonzalo et al., "Phosphoinositides Regulate Ciliary Protein Trafficking to Modulate Hedgehog Signaling," Dev. Cell., vol. 34, No. 4, pp. 400-409, Aug. 2015.
Garcia-Gonzalo et al., "Scoring a backstage pass: Mechanisms of cillogenesis and ciliary access," Journal of Cell Biology, vol. 197, No. 6, pp. 697-709, Jun. 2012.
Giladi et al., "Mitotic Spindle Disruption by Alternating Electric Fields Leads to Improper Chromosome Segregation and Mitotic Catastrophe in Cancer Cells," Scientific Reports, vol. 5, No. 1, pp. 1-16, Dec. 2015.
Goetz et al., "The primary cillum: a signalling centre during vertebrate development," Nature Reviews Genetics, vol. 11, pp. 331-344, May 2010.
Guadiana et al., "Arborization of dendrites by developing neocortical neurons is dependent on primary cilla and type 3 adenylyl cyclase," The Journal of Neuroscience, vol. 33, No. 6, pp. 2626-2638, Feb. 2013.
Hashimoto et al., "Subependymoma of the lateral ventricle—case report," Neurol. Med. Chir. (Tokyo), vol. 31, pp. 732-735, 1991.
Hoang-Minh et al., "Disruption of KIF3A in patient-derived glioblastoma cells: effects on ciliogenesis, hedgehog sensitivity, and tumorigenesis," Oncotarget, vol. 7, pp. 7029-7043, Feb. 2016.
Hoang-Minh et al., "PCM1 Depletion Inhibits Glioblastoma Cell Cillogenesis and Increases Cell Death and Sensitivity to Temozolomide1," Translational Oncology, vol. 9, Issue 5, pp. 392-402, Oct. 2016.
Hothi et al., "High-Throughput Chemical Screens Identify Disulfiram as an Inhibitor of Human Glioblastoma Stem Cells," Oncotarget, vol. 3, pp. 1124-1136, Oct. 2012.
International Search Report and Written Opinion issued in application PCT/IB2022/061550 dated Jan. 26, 2023.
Ishii et al., "Primary cilla safeguard cortical neurons in neonatal mouse forebrain from environmental stress-induced dendritic degeneration," PNAS, vol. 118, No. 1, p. e2012482118, Dec. 2021.
Karanam et al., "An overview of potential novel mechanisms of action underlying Tumor Treating Fields-induced cancer cell death and their clinical implications," International Journal of Radiation Biology, vol. 97, No. 8, pp. 1044-1054, Oct. 2020.
Kessler et al., "Effects of tumor treating fields (TTFields) on glioblastoma cells are augmented by mitotic checkpoint inhibition," Cell Death Discovery, 2018, vol. 4(77), pp. 1-10, SpringerNature, Basingstoke, United Kingdom.
Kim et al., "Tumor treating fields inhibit glioblastoma cell migration, invasion and angiogenesis," Oncotarget, vol. 7, No. 40, pp. 65126-65136, Oct. 2016.
Kirson et al., "Alternating electric fields arrest cell proliferation in animal tumor models and human brain tumors", Proceedings of the National Academy of Sciences, Jun. 12, 2007, vol. 104(24), pp. 10152-7.
Kirson et al., "Disruption of Cancer Cell Replication by Alternating Electric Fields," Cancer Research, vol. 64, pp. 3288-3295, May 2004.
Lam, "Histone deacetylase 6-mediated selective autophagy regulates COPD-associated cilia dysfunction," The Journal of Clinical Investigation, vol. 123, No. 12, pp. 5212-5230, Nov. 2013.
Lin et al., "Global analysis of H3K4me3 and H3K27me3 profiles in glioblastoma stem cells and identification of SLC17A7 as a bivalent tumor suppressor gene," Oncotarget, vol. 6, pp. 5369-5381, Jan. 2015.
Linder et al., "Dexamethasone Treatment Limits Efficacy of Radiation, but Does Not Interfere With Glioma Cell Death Induced by Tumor Treating Fields," Frontiers in Oncology, vol. 11, p. 715031, Jul. 2021.
Mehta et al., "Critical review of the addition of tumor treating fields (TTFields) to the existing standard of care for newly diagnosed glioblastoma patients," Critical Reviews in Oncology/Hematology, vol. 111, pp. 60-65, Mar. 2017.
Mirvis et al., "Primary cilium loss in mammalian cells occurs predominantly by whole-cilium shedding." PLOS Biology, vol. 17, No. 7, p. e3000381, Jul. 2019.
Moser et al., "Primary cillogenesis defects are associated with human astrocytoma/glioblastoma cells," BMC Cancer, vol. 9, p. 448, Dec. 2009.
Moser et al., "Ultrastructural characterization of primary cilia in pathologically characterized human glioblastoma multiforme (GBM) tumors," BMC Clinical Pathology, vol. 14, Articel 40, Sep. 2014.
Neuhaus et al., "Alternating Electric Fields (TTFields) Activate Cav1.2 Channels in Human Glioblastoma Cells," Cancers, vol. 11, p. 110, 2019.
Pampliega et al., "Functional interaction between autophagy and cillogenesis," Nature, vol. 502, No. 7470, pp. 194-200, Oct. 2013.
Parker et al., "Neonatal seizures induced by pentylenetetrazol or kainic acid disrupt primary cilla growth on developing mouse cortical neurons," Experimental Neurology, vol. 282, pp. 119-127, Aug. 2016.
Peixoto et al., "HDAC6-dependent ciliophagy is involved in ciliary loss and cholangiocarcinoma growth in human cells and murine models," American Journal of Physiology Gastrointestinal and Liver Physiology, vol. 318, No. 6, pp. G1022-G1033.
Praetorius et al., "Bending the MDCK Cell Primary Cilium Increases Intracellular Calcium," The Journal of Membrane Biology, vol. 184, No. 1, pp. 71-79, Dec. 2001.
Qiu et al., "Interaction of INPP5E with ARL13B is essential for its ciliary membrane retention but dispensable for its ciliary entry," Biology Open, vol. 10, Issue 1, bio057653, Jan. 2021.
Raleigh et al., "Cilla-Associated Oxysterols Activate Smoothened," Molecular Cell, vol. 72, pp. 316-327, Oct. 2018.
Reiter et al., "Genes and molecular pathways underpinning ciliopathies," Nature Reviews Molecular Cell Biology, vol. 18, pp. 533-547, Sep. 2017.
Romio et al., "OFD1 Is a Centrosomal/Basal Body Protein Expressed during Mesenchymal-Epithelial Transition in Human Nephrogenesis," vol. 15, No. 10, pp. 2556-2568, Oct. 2004, Abstract.

(56) References Cited

OTHER PUBLICATIONS

Rosenbaum et al., "Intraflagellar transport," Nature Reviews Molecular Cell Biology, vol. 3, pp. 813-825, Nov. 2002.
Sarkisian et al., "Detection of primary cilia in human glioblastoma," J. Neurooncol., vol. 117, No. 1, pp. 15-24, Mar. 2014.
Schneiderman et al., "TTFields alone and in combination with chemotherapeutic agents effectively reduce the viablity of MDR cell sub-lines that over-express ABC transporters," BMC Cancer, vol. 10, No. 229, 2010.
Shi et al., "HDAC6 Signaling at Primary Cilla Promotes Proliferation and Restricts Differentiation of Glioma Cells," Cancers (Basel), vol. 13, No. 7, p. 1644, Apr. 2021.
Shireman et al., "De novo purine biosynthesis is a major driver of chemoresistance in glioblastoma," Brain, vol. 144, No. 4, pp. 1230-1246, May 2021.
Shteingauz et al., "AMPK-dependent autophagy upregulation serves as a survival mechanism in response to Tumor Treating Fields (TTFields)," Cell Death Disease, vol. 9, p. 1074, Oct. 2018.
Silginer et al., "Biological activity of tumor-treating fields in preclinical glioma models," Cell Death and Disease, vol. 8, p. e2753, 2018.
Singla et al., "Ofd1, a human disease gene, regulates the length and distal structure of centrioles," Dev. Cell, vol. 18, No. 3, pp. 410-424, Mar. 2010.

* cited by examiner

METHODS OF REDUCING CILIOGENESIS WITH ALTERNATING ELECTRIC FIELDS

CROSS REFERENCE TO RELATED APPLICATIONS

This Application claims the benefit of U.S. Provisional Application 63/283,740, filed Nov. 29, 2021, which is incorporated herein by reference in its entirety.

Patents and publications cited herein and Appendix A are hereby incorporated by reference in their entirety.

BACKGROUND

The alternating electric fields (AEFs) discussed herein are similar to tumor treating fields (TTFields), and may be applied using hardware that is similar to Novocure's Optune® device, either at the same 200 kHz frequency that Optune uses, or at a different frequency (e.g., 50 kHz to 1 MHz). The size and shape of the transducer arrays that are used to apply the alternating electric fields to the subject's body will vary depending on the anatomical location to which the alternating electric fields are applied. The term "TTFields" as used herein and in the Figures and Appendix A is synonymous with the term "alternating electric fields."

High grade gliomas in adults, such as glioblastoma (GBM), usually have dismal prognoses due to the resistance and recurrence following all standard of care treatments. These treatments include a combination of surgical resection (if possible), irradiation, and temozolomide (TMZ) chemotherapy, the combination of which extends survival only a few months (1, 2), indicating novel treatments are urgently needed. One of the latest Food and Drug Administration-approved treatments for high grade glioma patients is Tumor Treating Fields (TTFields) (Optune), a device/electrode set that patients wear during their treatment that delivers low intensity (1-3V/cm), alternating high frequency (200 kHz) electric fields across the head. Combining maintenance treatment with TMZ, TTFields significantly increases overall survival several months beyond TMZ alone (3, 4). Thus, TTFields is considered a new standard of care (5). However, our understanding of how TTFields differentially targets gliomas over normal cells, interacts or enhances current therapies, or whether tumor cell characteristics predict sensitivity to TTFields remain unanswered questions.

The anti-tumor effects of TTFields do not occur via a single mechanism of action but rather a variety of cellular and molecular alterations (for review see: (6)). For example, TTFields disrupt the microtubular organization of mitotic spindle affecting normal cytokinesis and mitosis (7-9), as well as suppressing cell migration and invasion (10, 11). TTFields inhibit DNA damage repair and induce replication stress (12, 13). TTFields can induce autophagy (14) and promote immunogenic cell death (15). TTFields also change the cell membrane permeability to a greater extent in tumor cells compared to primary dermal fibroblasts (16). Such membrane changes may be linked to calcium channel activation and rapid calcium influx that occurs during TTFields (17). Altogether these factors may cumulatively result in reduced proliferative and invasive capacity of glioma cells and enhanced sensitization to current therapies.

SUMMARY

In one aspect the disclosure provides a method of determining susceptibility of cancer cells of a subject to treatment with alternating electric fields, the method including applying alternating electric fields to a first batch of cancer cells obtained or derived from a subject; ascertaining, after applying the alternating electric fields to the first batch, a first percentage of the cancer cells of the first batch that are ciliated; ascertaining a second percentage of a second batch of cancer cells obtained or derived from the subject that are ciliated, wherein the second batch was not exposed to alternating electric fields prior to ascertaining the second percentage; and determining that the cancer cells of the subject are susceptible to treatment with alternating electric fields if the first percentage is lower than the second percentage.

In an aspect, the determining includes determining that the cancer cells of the subject are susceptible to treatment with alternating electric fields if the percentage of the cancer cells of the first batch that are ciliated is at least 20% lower than the percentage of the cancer cells of the second batch that are ciliated.

In an aspect the frequency of the alternating electric fields is between 50 kHz and 1 MHz, 100 kHz to 500 kHz, or 150 kHz to 300 kHz. In an aspect, the frequency of the alternating electric fields is 200 kHz, 180 kHz or 120 kHz. In an aspect, the intensity of the alternating electric fields is 0.1 V/cm to 20 V/cm, 0.5 to 10 V/cm, 1 to 10 V/cm, 1.0 to 4 V/cm, or 1.0 to 2.5 V/cm (RMS) for at least a portion of the region to which the AEF is applied.

In an aspect, the percentages of the cancer cells that are ciliated are ascertained by imaging cancer cells, advantageously by confocal microscopy or light microscopy or RT-PCR. In another aspect, the percentages of the cancer cells that are ciliated are ascertained by determining a level of ARL13B or of OTD1 in the first batch and the second batch.

In one aspect, the disclosure provides a method of reducing the viability of cancer cells of a subject, by applying alternating electric fields to a first batch of cancer cells obtained or derived from a subject; ascertaining, after applying the alternating electric fields to the first batch, a first percentage of the cancer cells of the first batch that are ciliated; ascertaining a second percentage of a second batch of cancer cells obtained or derived from the subject that are ciliated, wherein the second batch was not exposed to alternating electric fields prior to ascertaining the second percentage; and applying alternating electric fields to the cancer cells if the first percentage is lower than the second percentage. In an aspect, the applying includes determining that the cancer cells of the subject are susceptible to treatment with alternating electric fields if the percentage of the cancer cells of the first batch that are ciliated is at least 20% lower than the percentage of the cancer cells of the second batch that are ciliated.

In an aspect, the frequency of the alternating electric fields is between 50 kHz and 1 MHz, 100 kHz to 500 kHz, or 150 kHz to 300 kHz. In an aspect, the frequency of the alternating electric fields is 200 kHz, 180 kHz or 120 kHz. In an aspect, the intensity of the alternating electric fields is 0.1 V/cm to 20 V/cm, 0.5 to 10 V/cm, 1 to 10 V/cm, 1.0 to 4 V/cm, or 1.0 to 2.5 V/cm (RMS) for at least a portion of the region to which the AEF is applied.

In an aspect, the alternating electric fields are applied for at least 12 hours, at least 24 hours, or at least 72 hours.

In an aspect, the method further includes administering a chemotherapeutic agent to the cancer cells. For example, the chemotherapeutic agent may be TMZ or a checkpoint inhibitor.

In an aspect, the disclosure provides a method of treating Huntington's disease in a subject in need of treatment, by applying alternating electric fields to a brain of the subject at a frequency between 50 kHz and 1 MHz. In an aspect the frequency of the alternating electric fields is between 50 kHz and 1 MHz, 100 kHz to 500 kHz, or 150 kHz to 300 kHz. In an aspect, the frequency of the alternating electric fields is 200 kHz, 180 kHz or 120 kHz. In an aspect, the alternating electric fields are applied for at least 12 hours, at least 24 hours, or at least 72 hours. In an aspect, the intensity of the alternating electric fields is 0.1 V/cm to 20 V/cm, 0.5 to 10 V/cm, 1 to 10 V/cm, 1.0 to 4 V/cm, or 1.0 to 2.5 V/cm (RMS) for at least a portion of the region to which the AEF is applied.

In one aspect, the disclosure provides a method of determining susceptibility of cancer cells of a subject to treatment with alternating electric fields, including applying alternating electric fields to a first batch of cancer cells obtained or derived from a subject; ascertaining, after applying the alternating electric fields to the first batch, an average length of a primary cilia of cancer cells of the first batch; ascertaining an average length of a primary cilia of cancer cells of the second batch; and determining that the cancer cells of the subject are susceptible to treatment with alternating electric fields if the average length of the primary cilia of the first batch is shorter than the average length of the primary cilia of the second batch.

In an aspect, the determining includes determining that the cancer cells of the subject are susceptible to treatment with alternating electric fields if the average length of the primary cilia of the first batch is at least 20% shorter than the average length of the primary cilia of the second batch.

In an aspect, the frequency of the alternating electric fields is between 50 kHz and 1 MHz, 100 kHz to 500 kHz, or 150 kHz to 300 kHz. In an aspect, the frequency of the alternating electric fields is 200 kHz, 180 kHz or 120 kHz. In an aspect, the intensity of the alternating electric fields is 0.1 V/cm to 20 V/cm, 0.5 to 10 V/cm, 1 to 10 V/cm, 1.0 to 4 V/cm, or 1.0 to 2.5 V/cm (RMS) for at least a portion of the region to which the AEF is applied. In an aspect, the alternating electric fields are applied for at least 12 hours, at least 24 hours, or at least 72 hours.

In an aspect, the average length of the primary cilia is ascertained by imaging cancer cells. In an aspect, the average length of the primary cilia is ascertained by confocal microscopy or light microscopy.

In one aspect, the disclosure provides a method of reducing the viability of cancer cells of a subject, including: applying alternating electric fields to a first batch of cancer cells obtained or derived from a subject; ascertaining, after applying the alternating electric fields to the first batch, an average length of a primary cilia of cancer cells of the first batch; ascertaining an average length of a primary cilia of cancer cells of the second batch; and applying alternating electric fields to the cancer cells in the subject if the average length of the primary cilia of the first batch is shorter than the average length of the primary cilia of the second batch.

In an aspect, the applying comprises determining that the cancer cells of the subject are susceptible to treatment with alternating electric fields if the average length of the primary cilia of the first batch is at least 20% shorter than the average length of the primary cilia of the second batch. In an aspect the frequency of the alternating electric fields is between 50 kHz and 1 MHz, 100 kHz to 500 kHz, or 150 kHz to 300 kHz. In an aspect, the frequency of the alternating electric fields is 200 kHz, 180 kHz or 120 kHz. In an aspect, the intensity of the alternating electric fields is 0.1 V/cm to 20 V/cm, 0.5 to 10 V/cm, 1 to 10 V/cm, 1.0 to 4 V/cm, or 1.0 to 2.5 V/cm (RMS) for at least a portion of the region to which the AEF is applied. In an aspect, the alternating electric fields are applied for at least 12 hours, at least 24 hours, or at least 72 hours.

In an aspect, the method further includes administering a chemotherapeutic agent to the cancer cells. For example, the chemotherapeutic agent may be TMZ or a checkpoint inhibitor.

DETAILED DESCRIPTION

Figure 1:
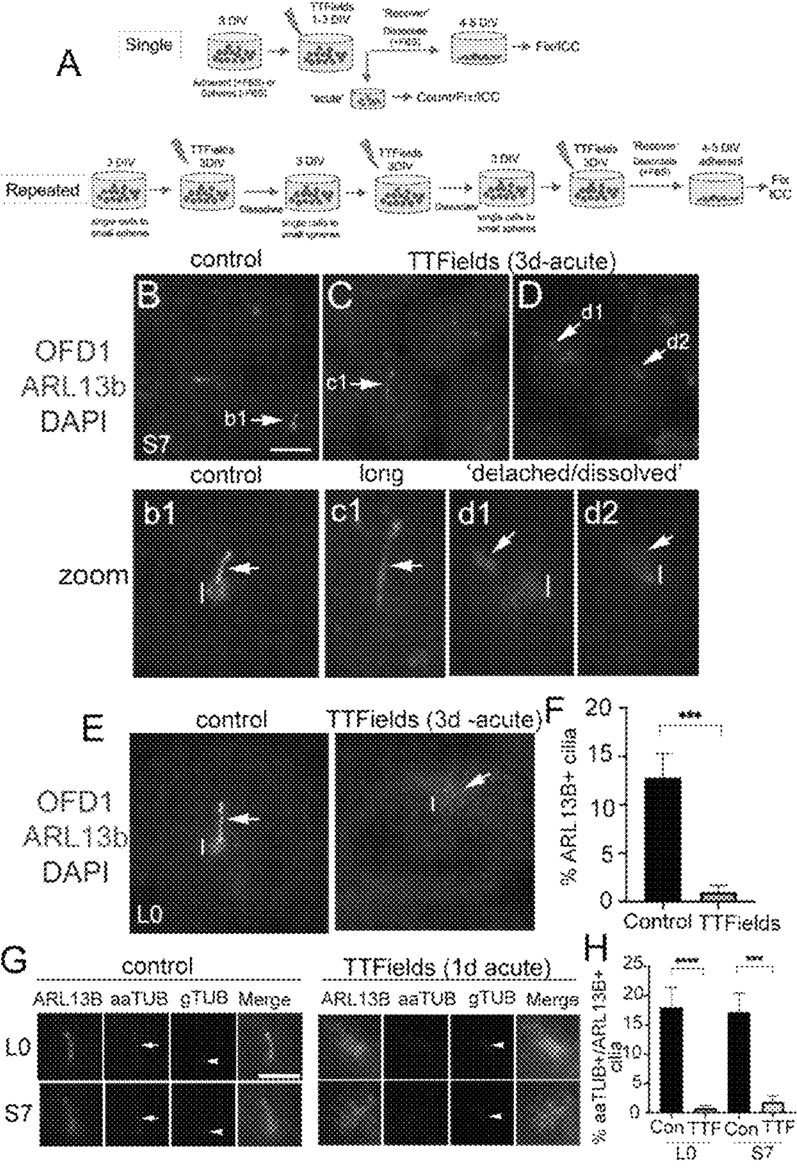
FIG. 1 shows ablation of primary cilia on patient-derived glioma cells by TTFields.

Many pathways impacted by TTFields are regulated by or involve signaling linked to the primary cilium (for review see: (18-20)). Primary cilia are non-motile, microtubule-based organelles extending from the mother centriole of the basal body. Cilia are disassembled so centrioles within the basal body can duplicate, segregate and be re-purposed for mitosis. Cilia are unsheathed by plasma membrane distinct from membrane of the cell body (21-24), and generally depend on intraflagellar transport machinery for their outgrowth and mobilize cargo anterogradely to the ciliary tip and retrogradely back to the cell body (25). At any given time, cilia are present on up to 30% or more of high-grade glioma cells (26). Nothing is known about how electrical field stimulation impact primary cilia on glioma cells. In human adipose-derived stem cells, brief exposures (4 hours/day) to low intensity (1V/cm), low frequency (1 Hz) were reported to induce osteogenesis via primary cilia (27). Electrical field-induced osteogenic responses were absent when ciliogenesis was inhibited using siRNA targeting an essential ciliogenesis gene intraflagellar transport 88 (IFT88)(27). Exposure to 16 Hz pulsed electromagnetic fields protected ciliary morphology against cigarette-smoke induced damage in osteoprogenitor cells (28). Thus, whatever role(s) primary cilia serve on glioma cells, they may be sensitive to or stimulated by the much higher therapeutic frequencies used in TTFields therapy.

The cilia on glioma cells may play a role in resistance to TMZ (29, 30). For example, cilia depletion mediated by CRISPR/Cas9 depletion of PCM1 or KIF3a, two ciliogenesis genes, sensitized GBM cells to TMZ (29). More recently, TMZ was shown to induce enhancer of zeste homologue 2 (EZH2) which targets the expression of ADP ribosylation factor 13b (ARL13B), a regulatory GTPase highly concentrated in glioma cilia (26, 31), as an adaptive mechanism that promotes chemoresistance (30). Knockdown of ARL13b/cilia using shRNA in patient derived xenografts in vivo, not only slowed tumor growth, but increased sensitivity to TMZ in vivo. Thus, if TTFields affects ARL13B or ARL13B' cilia, the sensitivity of glioma cells to TMZ could be enhanced. The goals of this study were to characterize whether and how TTFields at the clinical frequency (200 kHz) affect glioma ciliogenesis compared to normal neural cell types in vitro. We also examined how TMZ alone versus TMZ plus TTFields affects ciliogenesis and proliferation on both ARL13b$^+$ (ciliated) and ARL13B$^-$ (non-ciliated) glioma cell lines characterized previously (32). Finally, we explored whether TTFields affects ARL13B+ cilia in the patient tumor microenvironment.

Examples

1. Effects of Different Durations of TTFields on Low and High Grade Patient Glioma Cell Primary Ciliogenesis.

We exposed two patient-derived glioma cell lines, L0 (a grade IV glioblastoma) and S7 (a grade II glioma) that grow primary cilia (26, 29, 31-33) to TTFields. We used Novocure's Inovitro™ system to deliver low-intensity (1-4V/cm), 200 kHz electric fields to cultured cells which presumably mimic the type of fields delivered by the Optune® device in patients, similar to recent studies (16, 34). Generally, glioma cells were grown adherent (in serum) on coverslips or as free-floating spheres (without serum) for 3 days, then performed a single exposure to TTFields for up to 24 hours or 3 continuous days at which point we analyzed cells immediately ('acute') (FIG. 1A). For repeated TTFields exposures we dissociated cells after 3 days of continuous TTFields and repeated the cycle 2 more times (FIG. 1A). For recovery, after the last day of single or repeated TTFields, we dissociated spheres and cultured cells adherently (with serum) on coverslips and examined cells after 4-5 days.

After a single 3 days' exposure to TTFields, we immunostained cells for ARL13B and orodigital facial syndrome 1 (OFD1), a protein that concentrates around the basal body (35-37). In control S7 cells, ARL13B+ cilia were readily identifiable extending from OFD1+ basal bodies (FIG. 1B, b1). After TTFields, the presence of ARL13B+ cilia were largely undetected. Cilia that remained were typically elongated (FIG. 1C, ci), or appeared detached from (FIG. 1D, d1) or dissolved (FIG. 1D, d2) around the basal bodies. Most TTFields-treated cilia displayed reduced intensity of OFD1 around the basal body compared to control (FIG. 1*b*1, d1, d2). We observed similar phenomena in L0 cells (FIG. 1E). The appearance (FIG. 1E) and percent of ARL13B+ cilia (FIG. 1F) in L0 cells was significantly reduced. The effects of TTFields on glioma cilia can be seen within 24 hours post treatment. In both L0 and S7 cell lines there was a significant loss of ARL13B+ cilia after TTFields (FIG. 10A-F). To confirm TTFields is affecting the cilium and not just ARL13B localization along the ciliary membrane, we performed triple immunostaining to label a different component of cilia axoneme, acetylated-alpha tubulin (aaTUB) along with gamma-tubulin (gTUB) a microtubule component of the basal body/centriole, and ARL13B. In both L0 and S7 control cells, we found cilia that co-localized aaTUB+ and ARL13B+ extended from gTUB+ basal bodies (FIG. 1G). However, after TTFields, ARL13B puncta clustered around gTUB+ basal body/centrioles without obvious aaTUB+ axoneme extending from gTUB+ puncta (FIG. 1G). Quantification of cilia with both aaTUB+ and ARL13B+ cilia revealed significantly reduced frequencies after TTFields in the two cell lines (FIG. 1H), indicating that TTFields disrupt the integrity of the entire organelle.

The above observations show that TTFields effects on the cilia of glioma initiate within hours. Indeed, TTFields has been shown to disrupt glioma cell membrane permeability within the first hour of treatment (16). Thus, we examined the cilia axoneme and membrane 60 minutes and 6 hours after TTFields using antibodies against aaTub, gTUB, ARL13B and inositol polyphosphate-5-phosphatase E (INPP5e). INPP5e localizes to the ciliary membrane where it interacts with ARL13B (22, 38). We found that after 6 hours, cilia appeared longer than controls in both cell lines. The elongated ARL13B+ cilia displayed underlying colocalization with aaTUB+ suggesting that TTFields may stimulate a transient lengthening of the entire organelle within hours (FIG. 11A, C). We also observed some anomalies in the ciliary distribution of ARL13B and INPP5e staining. ARL13B and INPP5e seemed to distribute evenly along the ciliary axoneme in control, but after 60 min and 6 hours exposure to TTFields, the staining pattern appear clustered or polarized toward the proximal and distal tips of the cilium (FIG. 11A, B, C). In S7 cells we also observed unusual clusters of INPP5e surrounding the basal body after TTFields (FIG. 11B). Thus, in addition to a ciliary lengthening that precedes the loss of cilia, TTFields affects properties of the cilia membrane and surrounding base within hours of exposure in vitro.

The significant depletion of primary cilia by TTFields led us to ask if this effect was permanent. That is, would the frequency of ciliated glioma cells remain low if treatment is stopped and cells are allowed to recover? After single or repeated TTFields exposure, we plated cells in serum for 4-5 days, fixed, and immunostained for ARL13B and pericentriolar material 1 (PCM1), another protein that clusters around the basal body and centrioles in glioma cells (Hoang Minh 2016). In S7 cells, ARL13B+ cilia were detectable but appeared longer than control (FIG. 2A). The quantification confirmed cilia in TTFields groups were significantly longer than control (FIG. 2B). However, the frequency of ciliated glioma cells was not significantly changed (FIG. 2C). Similarly, in L0 cells, cilia were significantly longer after recovery from TTFields (FIG. 2D) but the frequency was unchanged (FIG. 2E). These data indicate that frequencies of ciliated glioma cells are restored after TTFields but are affected in a way that leads to elongation.

2. TTFields does not have the Same Impact on Normal Mouse Neural Cilia.

Considering the robust depletion of glioma cilia within 24 hours of TTFields (FIG. 1G,H, FIG. 10), we next asked whether cilia of normal primary neural cell types are similarly affected by TTFields. To test this, we cultured dissociated mouse embryonic cortices on glass coverslips for 11 days in vitro (DIV). At 11 DIV, we assigned coverslips as control or TTFields (24 hours or 3 days exposure). One advantage of this type of culture is that we can examine the effects of TTFields on cells that differentiate into various subtypes including astrocytes and neurons, marked by glial fibrillary acidic protein (GFAP) and neuronal nuclei (NeuN) expression respectively.

We first examined astrocyte cilia through a combined immunostaining for GFAP, ARL13B and pericentrin (Pcnt, a protein concentrated around the cilia basal body) (FIG. 3A, D). After 24 hours of TTFields, we did not observe significant differences in the frequency (FIG. 3B) or length (FIG. 3C) of astrocyte cilia. However, after 3 days of TTFields, there were significantly fewer ciliated GFAP+ cells (FIG. 3E), though the lengths of these cilia were comparable to control (FIG. 3F). These data show that, at least at acute timepoints after TTFields, astrocyte cilia are more resistant to TTFields than glioma cells.

Next we examined neuronal cilia by triple immunostaining for NeuN, type 3 adenylyl cyclase (AC3), an enzyme enriched in most neuronal cilia in the cortex (39-41), and Pcnt (42, 43) (FIG. 3G, J). After 24 hours of TTFields, we did not observe any significant changes on the frequency of neurons with AC3+ cilia (FIG. 3H), but the lengths of AC3+ cilia were significantly reduced (FIG. 3I). After 3 days of TTFields, both the frequency and length of AC3+ cilia on NeuN+ cells were significantly reduced compared to control (FIGS. 3K and L, respectively). The extent of the reduced ciliary frequency was 40% of control neurons, compared to about a 90% decrease in L0 cells after similar duration. Thus, neurons, especially after 24 hr of TTFields, appear more resistant though not completely spared from the effects of TTFields.

The neural cultures also contained populations of multiciliated cell types (presumably cells that differentiated into ependymal cells) and proliferating cells. However, the cells bearing tufts of cilia, detected by combination of ARL13B and Pcnt, appeared comparable after 24 hr (data not shown) and 3 days of continuous TTFields (FIG. 3M). A fraction of the cells in the culture were still Ki67+ suggesting they were still active in the cell cycle (FIG. 3N). However, amongst the Ki67+ cells (FIG. 3O) we did not observe significant change in the percentage of ciliated cells (FIG. 3P). Thus, TTFields spare the ability for multiciliated ciliated and cycling cells to form or maintain their cilia. Altogether these data suggest a differential sensitivity to TTFields between normal neural cell types and glioma cells.

3. TTFields-Induction of Autophagy and Death of Ciliated Cells Contribute to Cilia Depletion.

Figure 4A:
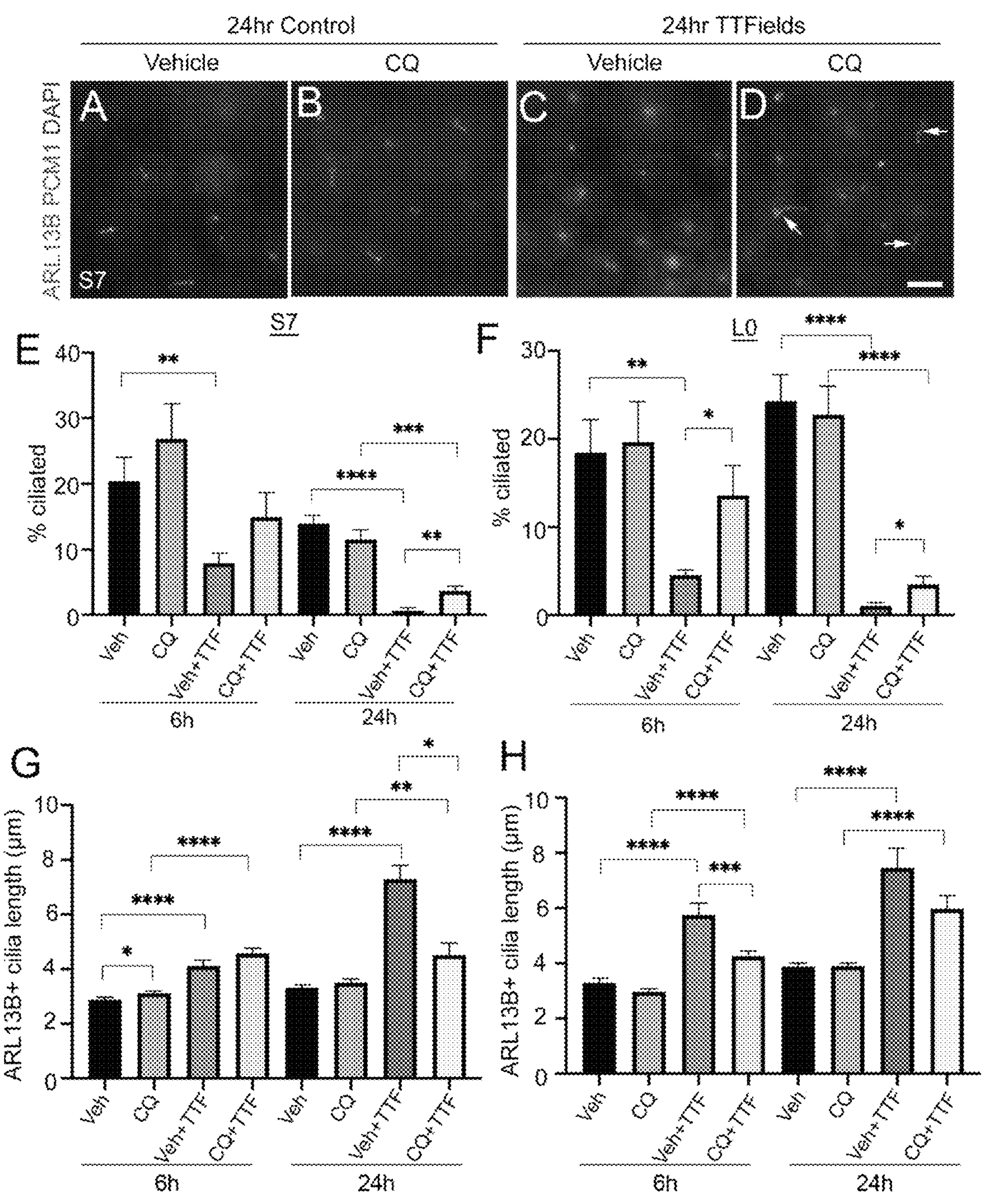
FIGS. 4*a* and 4*b* show chloroquine pretreatment partially prevents TTFields-induced loss of cilia.

What is the mechanism through which TTFields promotes rapid cilia loss in glioma cells? A number of factors and pathways promote cilia disassembly (44). Examples include calcium shock/influx (45), or autophagy activation (46), processes that have been shown to rapidly increase after TTFields onset (14, 17). We examined whether buffering extra/intracellular $Ca^{2+}$ by pre-treating cells with 600 mM EGTA or 1 μM BAPTA increase cilia frequency during TTFields, however we did not observe any prevention of cilia loss (data not shown). We then examined if the autophagy pathway activation at cilia was involved, in part because the reduced OFD1 expression we observed around the basal bodies after TTFields (FIG. 1), is a potential indicator of autophagy activation (37, 47). In addition, we observed microtubule-associated proteins 1A/1B light chain 3B (LC3B) and phospho-AMPK (pAMPK) recruitment to basal bodies after single and repeated TTFields (FIG. 12) consistent with reports that autophagy proteins are recruited to primary cilia (46, 48). Thus, we pre-treated S7 and L0 cells 30 minutes before TTFields induction with vehicle or autophagy inhibitor, chloroquine (CQ) (20 μM) and fixed cells after 6 or 24 hours, and analyzed the frequency and length of cilia. A concentration of 20 μM CQ was selected because it inhibited autophagy pathway activation in response to TTFields in U87 and other glioma cell lines (14). We found that S7 glioma cells pre-treated with CQ 30 minutes before TTFields led to a significant increase in the percent of ciliated cells after 24 hours compared to control (FIG. 4A-D, E). The TTFields-induced increase in cilia length in S7 cells was also reduced by CQ at 24 hr (FIG. 4G). In L0 cells, we observed significantly more ciliated cells after 6 and 24 hours pretreatment with CQ and exposed to TTFields (FIG. 4F). In addition cilia length of CQ-treated L0 cells at 6 hours was significantly reduced compared to vehicle after 6 hours TTFields (FIG. 4H) suggesting autophagy activation may be underlying the observed elongation after TTFields. It is noteworthy that in both S7 and L0 cells, 6 hours of TTFields was sufficient to observe significant cilia elongation. Further, because CQ did not fully restore the frequency of cilia to control suggests that either CQ may not inhibit autophagy in all cells, or that the activation of autophagy may represent one of the factors resulting in TTFields-induced cilia depletion.

To more directly examine how ciliated cells respond during TTFields, we transfected L0 and S7 cells with a two cDNA constructs encoding ARL13B:GFP and OFD1:mCherry allowing us to track isolated cells displaying ARL13B:GFP+ cilia with OFD1:mCherry+ clusters around the basal body overnight (FIG. 13A). We live imaged cells up to 24 hours after transfection using Novocure's inovitro LIVE imaging system. Notably hours after TTFields onset we observed ciliated L0 cells that appeared to die (FIG. 13B, C), with similar observations in S7 cells during TTFields (FIG. 13D). These data show that TTFields may have a direct impact on the survival and proliferation of ciliated glioma cells or cells that derive from ciliated glioma cells.

4. TMZ-Induced Ciliogenesis is Blunted by TTFields.

The survival benefit promoted by TTFields in patients occurs during TMZ maintenance therapy (3, 4). TMZ has recently been reported to increase the frequency and length of ARL13B+ cilia patient-derived glioblastoma cells (30). Thus, we asked if the effects of TTFields on cilia would be similar in the presence of TMZ chemotherapy. The effects of TMZ on glioma ciliogenesis have not been extensively analyzed with respect to different cell lines, different concentrations and durations of exposure. Thus, we first examined how different durations and concentrations of TMZ, doses lower than those typically used to kill cells in in vitro assays, affect the frequency and length of ARL13B+ glioma cilia in our cell lines.

Figure 5A:
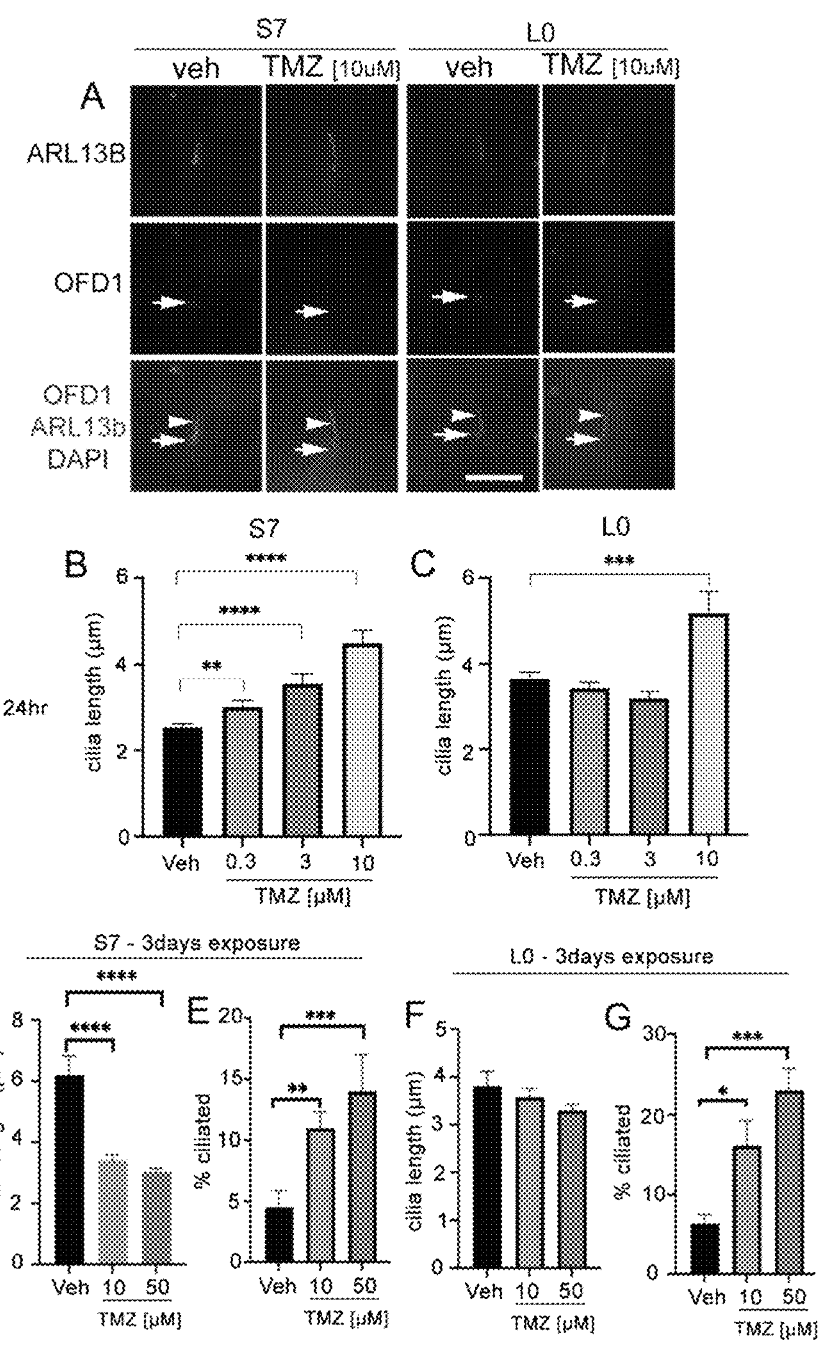
FIGS. 5*a* and 5*b* show TMZ stimulates ciliogenesis in L0 and S7 cells.
Figure 5B:
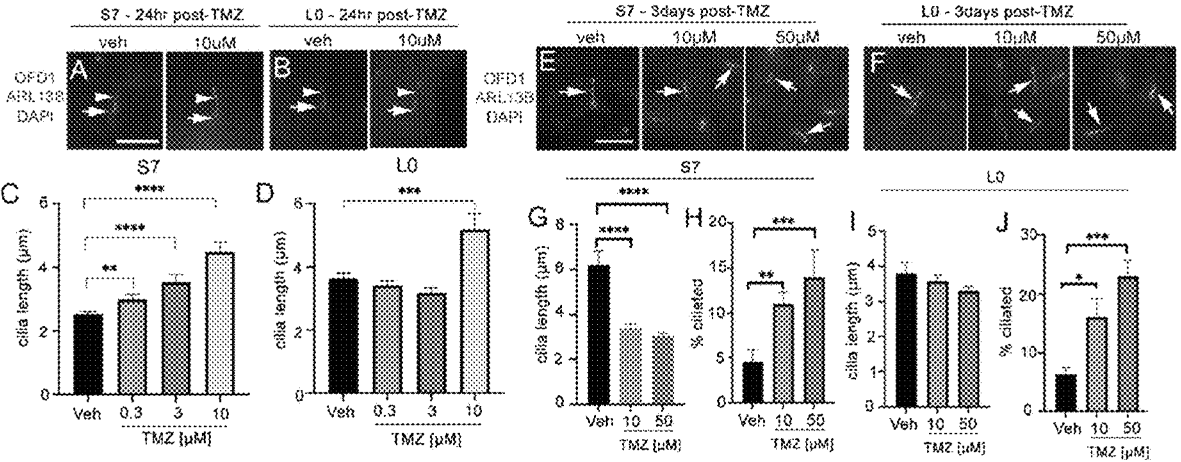

In L0 and S7 cells, 24 hours treatment with 10 μM TMZ appeared to elongate primary cilia in both cell lines (FIG. 5A). In S7 cells, we observed a dose-dependent effect with 0.3, 3 and 10 μM TMZ sufficient to increase cilia length after 24 hours exposure (FIG. 5B). In L0 cells, we found that 10 μM TMZ significantly increased the length of ARL13B+ cilia compared to lower TMZ concentrations and vehicle (FIG. 5C). After 3 days of exposure to TMZ (a duration chosen because we performed 3 days of continuous TTFields), we found that in 57 cells, 10 μM and 50 μM TMZ significantly reduced the length of cilia (FIG. 5D) but significantly increased the frequency of ciliated cells (FIG. 5E). However, 3 days of TMZ exposure in L0 cells did not affect cilia length after 10 μM or 50 μM (FIG. 5F), but like S7 cells significantly increased the frequency of ciliated L0 cells as in S7 cells (FIG. 5G). These results support results of recent studies (30) and show that TMZ is capable of stimulation the elongation of ARL13B+ cilia, at least acutely, and increasing the frequency of ciliated glioma cells.

Figure 6:
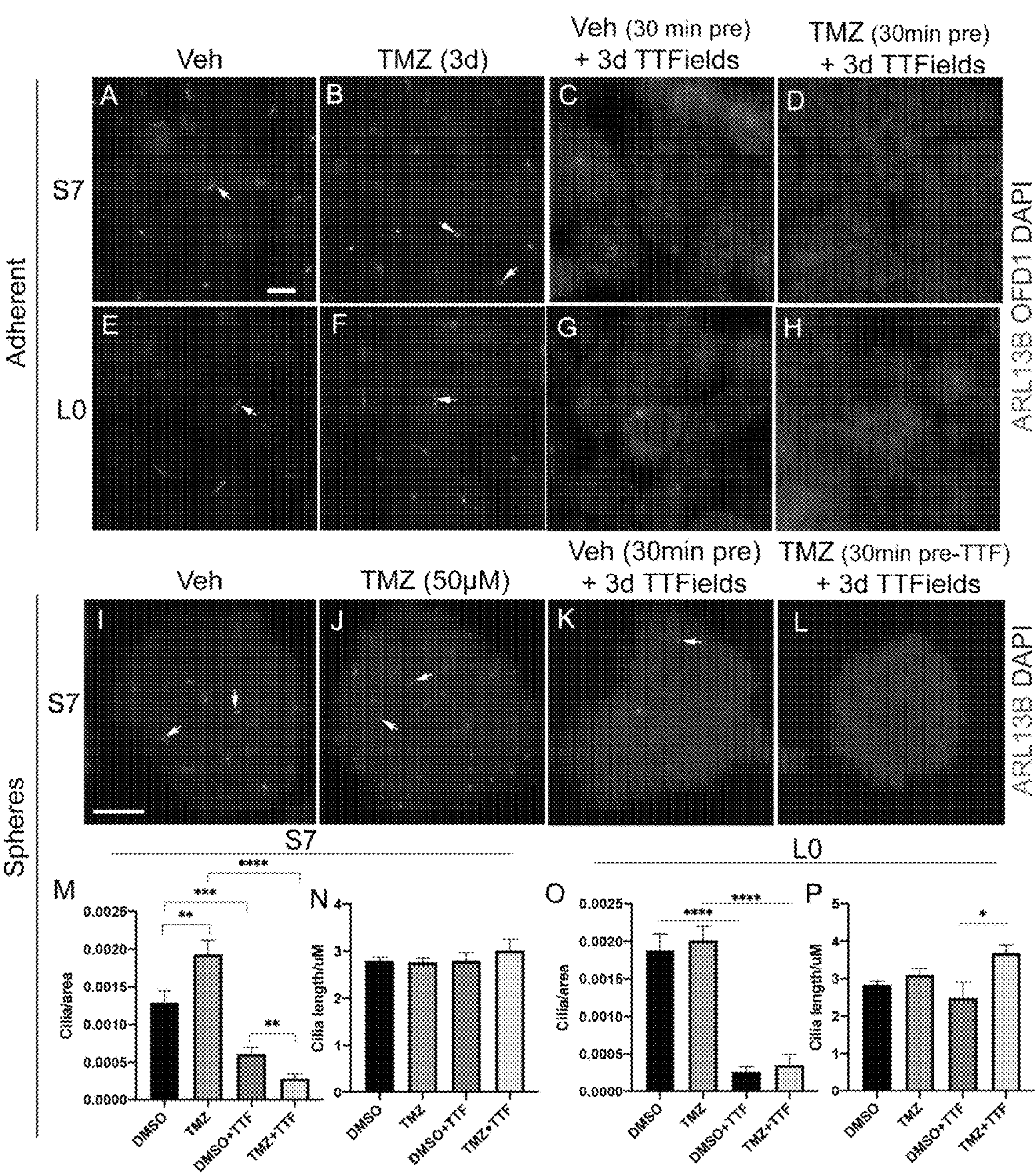
FIG. 6 shows applying TTFields blocks the TMZ-mediated increase in ciliogenesis.

Since TMZ generally stimulates ciliogenesis, and TTFields inhibits it, we examined glioma cilia with a combination of these treatments in adherent cells and spheres (FIG. 6). First, we pre-treated adherent S7 and L0 cells with concentrations of TMZ that stimulated ciliogenesis about 30 minutes before a 3 days exposure to TTFields initiation. We found that in both adherent S7 (FIGS. 6A-D) and L0 (FIG. 6E-H) cells, ciliogenesis was not observed in the presence of TMZ plus TTFields (FIG. 6D, H). We also examined if TTFields had the same effect in gliomaspheres. We cultured S7 and L0 spheres for 3 days, and then treated them for 3 days with vehicle, 50 μM TMZ, TTFields, or TTFields plus 50 μM TMZ (added 30 min before onset) (FIG. 61-L). We then collected and fixed spheres, sectioned and immunostained them for ARL13B. For each sphere, we normalized the number of cilia to the area of the sphere. In S7 cells, we found that TMZ alone increased the frequency of cilia (FIG. 6M), consistent with what we observed in adherent cells (FIG. 5E). As expected, TTFields significantly reduced the frequency of cilia in the spheres but TMZ-induced increase did not occur in the presence of TTFields (FIG. 6M). Interestingly we did not observe a change in the length of cilia across groups (FIG. 6N). Unlike S7 cells, TMZ alone did not increase the frequency of cilia in L0 spheres (FIG. 6O). However, like S7 cells, TTFields reduced the frequency of cilia in the L0 spheres which was not enhanced by the co-treatment of TMZ plus TTFields (FIG. 6O). Together, these results show that TTFields disrupt the pro-ciliogenic effects of TMZ.

5. TTFields Ablation of ARL13B+ Cilia is Associated with Enhanced TMZ Efficacy.

Figure 7A:
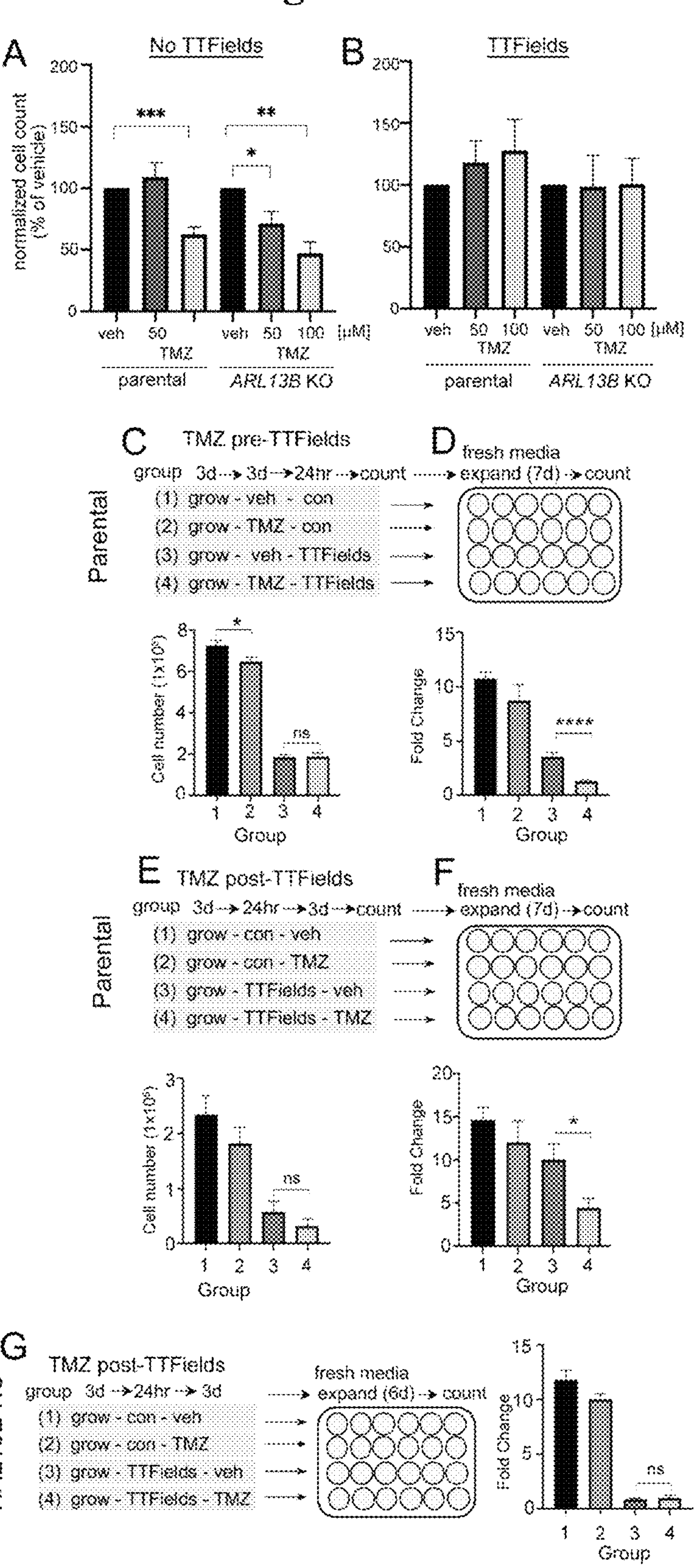
FIGS. 7*a* and 7*b* show ARL13B+ cilia are linked to TMZ resistance and proliferation after TMZ and TTFields treatment.
Figure 7B:
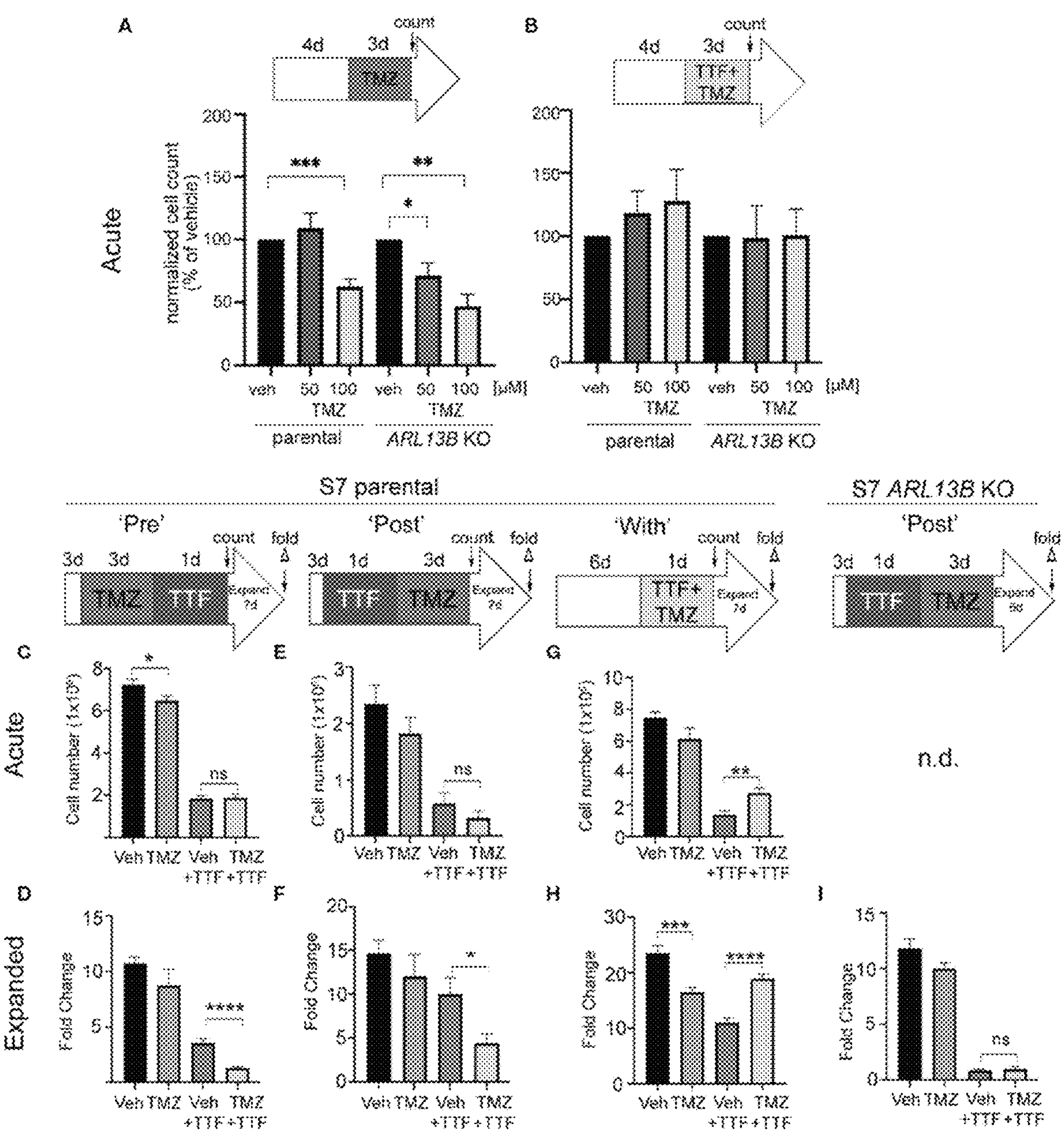

Previously we found that deleting key ciliogenesis genes (e.g. PCM1, KIF3A) enhanced sensitivity of glioma cells to TMZ (29). Similarly, glioma cells expressing ARL13B shRNA, which depleted cilia, were more sensitized to TMZ in vitro and in vivo (30). Using our S7 glioma transgenic cell line depleted in ARL13B and cilia using CRISPR/Cas9 (32), we examined how these cells proliferated in response to TMZ, TTFields, or TMZ plus TTFields. After four days of growing S7 parental or ARL13B KO spheres, we treated them with vehicle, 50 or 100 μM TMZ in the absence or with 3 days of TTFields. In parental S7 cells, proliferation was reduced in 100 μM TMZ group (FIG. 7A). However, in ARL13B KO cells, proliferation was significantly reduced at 50 μM and 100 μM TMZ groups (FIG. 7A), consistent with results of previous studies that ARL13B+ cilia are associated with resistance to TMZ. However, when we co-treated S7 parental or ARL13B KO cells with TMZ with TTFields, there was no added toxicity in either group (FIG. 7B). This suggests cilia ablation by TTFields or thru genetic means, the co-treatment of TMZ and TTFields may not lead to additive toxicity.

Since we did not observe added acute toxicity following TMZ and TTFields co-treatment in S7 parental cells, we wondered if the treatment order or treatment effect could be delayed. We reasoned that stimulating ciliogenesis with TMZ might render more cells susceptible to TTFields, and/or that TTFields suppression of ciliogenesis may sensitize glioma cells to TMZ. To test this, we administered TMZ before (PRE) or TMZ after (POST) a 24 hr window of TTFields. In the PRE-experiment, we found that although the acute numbers of TMZ-TTFields-treated cells were similar to vehicle-TTFields (i.e., group 3 vs group 4 in FIG. 7C), the fold expansion of TMZ-TTFields treated cells seven days after treatment was significantly reduced compared to veh-TTFields (i.e., group 3 vs group 4 in FIG. 7D). In the POST-experiment, we also did not observe an acute reduction of TTFields-TMZ treated cells compared to control (i.e., group 3 vs group 4 in FIG. 7E), but did observe a significant reduction of TTFields-TMZ treated cells seven days after treatment (group 3 vs group 4 in FIG. 7F). Thus, TMZ pre- or post-TTFields slows tumor cell recurrence. We next asked if this interaction is linked or dependent on ARL13B+ cilia. Since there was a significant effect of giving TMZ before or after TTFields on parental cells, we chose the latter, and examined fold expansion of S7 ARL13b KO cells for 6 days TTFields-TMZ treatment (FIG. 7G). However, there was no significant difference in the expansion of TTFields-TMZ-treated and TTFields-Veh treated ARL13B KO cells (FIG. 7G, compare group 3 vs group 4). These results show the interaction between TMZ and TTFields on subsequent tumor cell expansion in vitro is linked to or dependent on ARL13b$^{+}$ cilia.

6. TTFields Disrupt Primary Cilia in Patient Tumors Ex Vivo.

Figure 14:
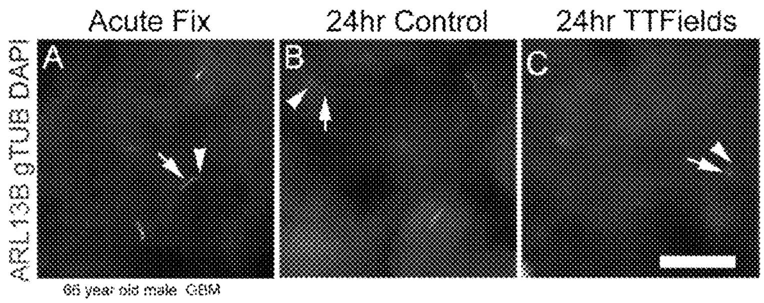
FIG. 14 shows loss of cilia in a glioblastoma biopsy treated with TTFields ex vivo.
Figure 15:
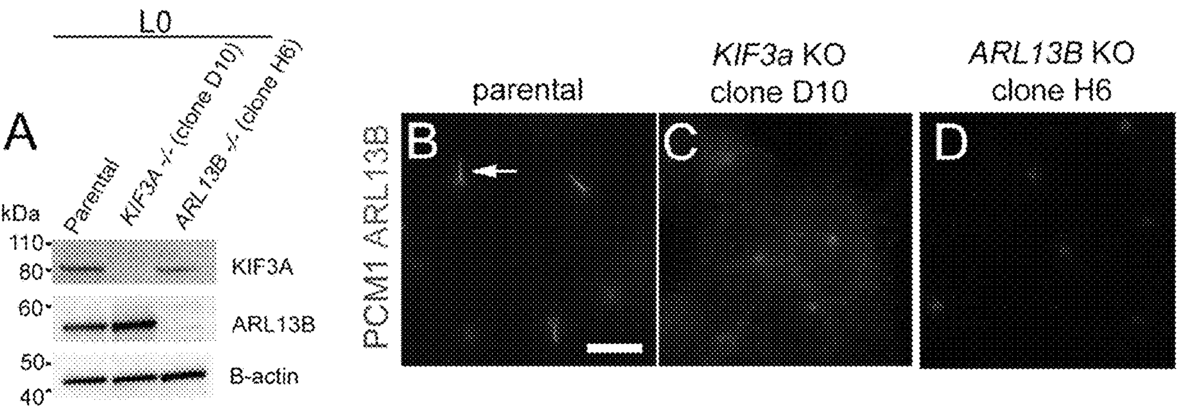
FIG. 15 shows generation of glioma lines lacking ARL13B/cilia.

Lastly, we asked if the effects of TTFields on cilia in adherent or spheres of glioma cells occur within the patient tumor microenvironment. To test this, we divided fresh biopsy samples into 3 groups: immediate/acute fixation, 24 hr control or 24 hr of TTFields. We then fixed, and immunostained cryosections of biopsies (FIG. 8A). First we examined a subependymoma (a grade 1 glioma), a tumor type reported to possess cilia (49). We found that ARL13B+ cilia extending from OFD1+ basal bodies were readily detectable in control (FIG. 8B) whereas we only clearly observed OFD1+ basal bodies in the TTFields treated biopsy (FIG. 8C). We also received newly diagnosed GBM biopsies from a 34-year-old male and 66-year-old male which we treated similarly except immunostained basal bodies/centrioles with gTUB and cilia with ARL13B antibodies. We observed gTUB+ basal bodies with ARL13B+ cilia in acutely fixed tissue and in overnight control (FIG. 8D, E, G), whereas the cilia appeared blunted or generally reduced in TTFields treated tissue (FIG. 8F, G). Similar observations were made in a 66-year-old male GBM biopsy exposed to 24 hr of TTFields (FIG. 14). These data are consistent with our cultured adherent cells and gliomaspheres, and indicate that TTFields disrupts ARL13B+ ciliated tumor cells within the tumor.

DISCUSSION

We show that TTFields significantly impact the ability of glioma cells to maintain their primary cilium. Low and high grade glioma cells disassemble their cilia shortly after TTFields, though the population is not completely eliminated because ciliated cells reappear at similar frequencies. The mechanism leading to cilia loss appears to involve a combination of autophagy activation and death of ciliated cells. Surprisingly, TTFields does not similarly impact the cilia of various normal neural cell types, pointing to one aspect of glioma biology that may be differentially sensitive to TTFields. Further, TMZ-induced increase in ciliated glioma cells is inhibited by TTFields. This is of potential significance because ARL13B-mediated signaling associated with glioblastoma cilia is linked to both tumor growth and TMZ sensitivity in vivo (30). Thus, the disruption of cilia by TTFields may help enhance TMZ efficacy, or help eliminate a population of treatment-resistant cells. The TTFields-mediated changes in cilia within patient tumors indicates that tumors containing high levels of ciliogenesis could be more receptive to TTFields and TMZ.

How does TTFields lead to glioma primary cilia dismantling? Within hours, TTFields triggers axonemal elongation with accompanying changes in the distribution of membrane proteins along the ciliary membrane proteins, culminating in the loss of the cilia. The re distribution of ciliary membrane-associated proteins may be due to TTFields effects on membrane permeability reported to occur during the same timescale (16). It is not clear if TTFields causes cilia to be absorbed back into the cell, shed into the extracellular milieu, or both? Most mammalian cilia appear to disassemble by shedding the whole cilium (50, 51). However, live imaging studies of glioma cells during TTFields support a withdrawal or absorption back into the cell process as we did not observe cilia detachment during live imaging. Whatever the mechanism of cilia loss after TTFields, the changes in cilia can serve as a biomarker of TTFields efficacy in the tumor. Although TTFields eliminates cilia/ciliated glioma cells, they grow back at the same frequency though longer if treatment is stopped. We do not know if the regrown cilia are from the same cells, or represent a new population of ciliated cells, which could potentially be addressed via extended live imaging during and after TTFields. The ciliary lengthening on recovered cells could be due to elevated autophagy pathway activation, which has been shown to elongate cilia (37). CQ has been observed to reduce the autophagy-mediated increase in cilia length on human kidney proximal tubular cells (52), which is further supported by our observation that CQ reduces the TTFields-induced lengthening (FIG. 4G, H).

Autophagy activation may represent one contributing factor in the disappearance of cilia after TTFields, since CQ pre-treatment did not fully restore the frequency of ciliated cells. TTFields may trigger many other factors that promote cilia removal. It is possible only a fraction of the cilia are removed by autophagy. HDAC6-mediated autophagy can result in 'ciliophagy', in mouse tracheal epithelial cells and cholangiocarcinoma cells (46, 53), and thus some glioma cilia may be driven by HDAC6 mediated autophagy whose signaling at cilia is a key regulator of glioma cell proliferation (32). Whatever the mechanism of autophagy linked to glioma cilia, it is unclear whether it is promoting or reducing cell survival. However, the link to autophagy is noteworthy as TTFields activation of autophagy appears to have dual significance. On one hand it may drive the death of cells (11), or alternatively promote activation of pathways that allow cells to resist TTFields (14). A scenario in which the ciliated glioma cells die by TTFields favors the former, whereas if glioma cells re-grow their cilia (supporting the return of cilia frequency) favor the latter. Alternatively, there could be a mixture of these scenarios that requires further study.

It is not clear why normal differentiating or proliferating neural cilia are less affected by TTFields. It is possible normal mouse neural cell type plasma membrane are more impervious to or recover quicker from the membrane permeating effects of TTFields than glioma ciliary membranes. For example, normal human fibroblast membranes were less perforated by TTFields than glioma cells (16). Neurons and glia however were not completely spared as cells showed lower frequencies with 3 days of exposure. However, the degrees of changes were far less than glioma cells. For example, neuronal cilia frequencies after 3 continuous days of TTFields were reduced by 40% compared to control whereas the ciliary frequency in glioma cells was reduced by 90%. The preservation of cilia from this stress could be cytoprotective. For example, primary cilia on neurons were recently reported to prevent neurite degeneration in developing cortical neurons after exposure to stressors in vivo including alcohol and ketamine (54). Similarly in normal glia, it was reported that hedgehog mediated signaling thru primary cilia promote cell survival in stressed in vitro conditions (55). Thus, the retention of cilia on neurons and glia may help protect against stress induced by TTFields. The extent to which TTFields affects tumor cells and normal neural cilia in the human brain will require post-mortem analyses.

Our findings indicate that TTFields could help eliminate or suppress TMZ-resistant cell types. TMZ can lead to increased expression of ARL13B and an interaction between ARL13B and the purine biosynthesis pathway as a mechanism to drive TMZ chemoresistance in glioblastoma (30). Thus, TTFields targeting of cilia or ciliated glioma cells may enhance TMZ toxicity. Given the opposing effects on TMZ and TTFields on ciliogenesis, we explored the effects of different order of these treatments and found that the interaction on subsequent proliferation does not depend on cells exposure to TMZ before or after TTFields. However, we observed a dependence on ARL13b/cilia following this combined treatment. Whether TMZ and TTFields have converging actions at the cilium remains unclear. Both treatments appear capable of stimulating autophagy (14, 56, 57), yet their effects on ciliogenesis appear opposite. Nevertheless, autophagy pathway inhibitors during or subsequent to these treatments could help target cells that clearly survive both treatments.

Our study indicates that gliomas with enhanced ciliogenic potential are more receptive to TTFields therapy, a cellular susceptibility that may come with tradeoffs. A tumor containing more ciliated proliferating cells may be more impacted by TTFields than tumors with few ciliated cells. However, a complete or sustained ablation of cilia may generate cell offspring that are mutated or transform into other resistant cell types. Indeed, some GBMs and older glioma cell lines are or become cilia-devoid (26, 58, 59). In medulloblastoma, loss of cilia mediated due to ablation of OFD1 can lead to SMO inhibitor treatment resistance and formation of 'persister-like' states that support tumor recurrence (60).

Materials and Methods

Cell Culture

L0 (grade IV glioblastoma from a 43 year old male) and S7 (grade II glioma from a 54 year old female with EGFR amplification) cell lines were isolated and maintained as previously described (26, 61, 62) (63). ARL13B and KIF3A-deficient L0 and S7 cells were generated using CRISPR/Cas9 as previously described (32). L0 and S7 cells were grown as floating spheres and maintained in NeuroCult NS-A Proliferation medium and 10% proliferation supplement (STEMCELL Technologies; Cat #05750 and #05753), 1% penicillin-streptomycin (Thermofisher, Cat #15140122), 20 ng/ml human epidermal growth factor (hEGF) (Cat #78006), and 10 ng/ml basic fibroblast growth factor (bFGF) (Cat #78003). For S7 cells, the media was supplemented with 2 μg/ml heparin (Cat #07980). All cells were grown in a humidified incubator at 37° C. with 5% $CO_2$. When cells reached confluency, or spheres reached approximately 150 μm in diameter, they were enzymatically dissociated by digestion with Accumax (Innovative Cell Technologies; Cat #AM-105) for 10 min at 37° C. For human cells grown on glass coverslips, NeuroCult NS-A Proliferation medium was supplemented with 10% heat inactivated fetal bovine serum (FBS) (Cytiva, Cat #SH30070.03H1).

Primary neural cultures were similar to previously described (Shi et al, Dagra et al 2021). Briefly, acutely micro-dissected C57/BL6 mouse cortices from postnatal day 0-2 pups were dissected into Gey's Balanced Salt Solution (Sigma-Aldrich, Cat #G9779) at ~37° C. under oxygenation for ~20 min. Dissociated cells were triturated with pipettes of decreasing bore size, pelleted by centrifugation at 1,500 rpm for 3-5 min, and resuspended and plated in glial medium containing DMEM (Cytiva HyClone, Cat #SH3002201), FBS (Gemini BioProducts, Cat #50-753-2981), insulin (Sigma-Aldrich, Cat #15500), Glutamax (Gibco, Cat #35050061) and Penicillin-streptomycin (Gibco, Cat #15140122). Cells were plated at a density of 80,000 cells/coverslip on 12-mm glass coverslips coated with 0.1 mg/ml poly-D-lysine followed by 5 μg/ml laminin in minimal essential medium. After approximately 2 hrs, cells were supplemented with 2 mL neuronal media containing Neurobasal A (Gibco, Cat #10888022) supplemented with B27 (Gibco, Cat #A3582801), Glutamax (Gibco, 35050061), Kynurenic acid (Sigma Aldrich, Cat #K3375), and GDNF (Sigma Aldrich, Cat #SRP3200). Every 4 days, half of the media was replaced with fresh neuronal media as described above but lacking kynurenic acid and GDNF. On DIV12, coverslips were transferred into TTFields dishes and fixed after 24 hrs or 3 days after treatment as described below.

TTFields Induction and Time-Lapse Imaging

For adherent and spheres, $5\times10^4$ cells were seeded in 2 ml growth media with or without 10% FBS, respectively. Adherent cells, spheres or biopsies were placed in TTFields ceramic dishes, each dish approximately the size of a single well of a 6-well plate, and mounted into inovitro™ base plates (Novocure Ltd., Haifa, Israel). The base plates were connected to a power generator which delivered TTFields at frequency of 200 kHz (1-4V/cm). During TTFields treatment, cells were maintained in an incubator (ESCO Technologies, Horsham, PA) with the ambient temperature between 18-22° C. with 5% $CO_2$ and a target temperature of 37° C. inside each ceramic dish. Treatment duration are as indicated but ranged from 1 to 72 hours for a single treatment. To prevent media evaporation during TTFields, parafilm was placed over each TTFields ceramic dish. In between repeated exposures or for recovery experiments, cells were dissociated and transferred back to a regular incubator. Control samples were grown at 37° C. in 5% $CO_2$ in 6 well plates. In some experiments, we pretreated cells before TTFields with either vehicle, or specified drugs. Unless otherwise stated, data in each experiment were pooled from at least 4 dishes per condition and per time-point.

For time-lapse imaging combined with TTFields, we plated 50,000 cells in 57/L0 media supplemented with 5% FBS into 35 mm glass bottom culture dishes (Ibidi, cat #81158) which were maintained at at 37° C. in 5% $CO_2$. Twenty four hours before imaging at about 70% confluency, cells were transfected with 500 ng total cDNA/dish of pDest-Ar113b:GFP (gift from T. Caspary) and pCMV-myc/mCherry:hOFD1 (Vectorbuilder.com, vector ID: VB201119-1128fyp) using Lipofectamine 3000 (Life Technologies; Carlsbad, CA, cat #L3000015). A TTFields-delivering ceramic insert was placed into the culture dish and connected to a generator that delivered TTFields at a frequency of 200 kHz and a target temperature of 37° C. inside each dish. Imaging was conducted on an inverted Zeiss AxioObserver D1 microscope using a Zeiss 40×/0.95 plan Apochromat air objective. The microscope stage was equipped with a Tokai Hit stage incubation system that maintained a humid environment and ambient temperature of 22-23° C. and 5% $CO_2$. Baseline images were captured every minute, whereas after TTFields onset, images were collected every 5 minutes with exposure times ranging in duration from 400 to 750 msec (EGFP) and 300-400 msec (Cy3) per image. Image acquisition and processing were performed using Zeiss ZEN software.

Ex-Vivo Culture and TTFields-Treatment

In accordance with our institutional IRB protocol (#201902489), we collected several fresh, surgically-resected tumor biopsies that were subsequently pathologically confirmed. Within 1 hour of the resection, biopsies were taken to the laboratory, and dissected into several pieces using a sterile scalpel blade. Tissues were immediately fixed and/or transferred into 2 mL of S7 media for culture at 37° C. in 5% $CO_2$ or transferred into TTFields dishes for a 24 hour exposure as described above. Following TTFields, control and treated samples were fixed and prepared as described above.

Cell Growth, Viability Assays

For cell proliferation assay, cells ($2.5\text{-}5\times10^4$) were seeded in 2 ml of growth media per well in 6-well plates, or in 1 ml of growth media per well in 24 well plates for indicated duration. Cells were then treated with various drugs including chloroquine (CQ) (Sigma; Cat #50-63-5) (20 μM diluted in sterile water), temozolomide (TMZ) (Sigma; Cat #85622-93-1) (0.3 to 100 uM diluted in DMSO), 1,2-bis(o-aminophenoxy)ethane-N,N,N',N'-tetraacetic acid (BAPTA) (Sigma; Cat #126150-97-8) (1 μM diluted in DMSO), or ethylene glycol-bis(β-aminoethyl ether)-N,N,N',N'-tetraacetic acid (EGTA)(Sigma; Cat #67425) (0.6 mM diluted in DMSO). After indicated treatment durations, cells were enzymatically dissociated and replaced in 1× phosphate-buffered saline (PBS). Total cell counts were collected using a Bio-Rad TC20 automated cell counter. Bar graphs show the mean (+/− SEM) and were analyzed statistically using analysis of variance (ANOVA).

Immunostaining

For immunocytochemical (ICC) and immunohistochemical (IHC) analyses, samples were fixed at indicated time-points with 4% paraformaldehyde in 0.1 M phosphate buffer (4% PFA) for 30 min or ice-cold methanol for 15 minutes (ICC) to 1 hour (IHC) and washed with 1×PBS. Spheres or biopsies were cryoprotected in 30% sucrose in PBS followed by a 1:1: 30% sucrose and optimal cutting temperature compound (OCT) (Fisher Healthcare, #4585), frozen in OCT over liquid N2 and cryosectioned at 16 μm. Samples were stained for the indicated primary antibodies (Table 1). Samples were incubated in blocking solution containing 5% normal donkey serum (NDS) (Jackson Immunoresearch; Cat #NC9624464) and 0.2% Triton-X 100 in 1×PBS for 1 hour and then incubated in primary antibodies with 2.5% NDS and 0.1% Triton-X 100 in 1×PBS either for 2 hours at room temperature (RT) or overnight at 4° C. For samples stained sequentially with mouse antibodies against gamma- and acetylated alpha-tubulin, samples were blocked with donkey anti-mouse IgG Fab fragments (20 μg/ml: Jackson Immunoresearch: Cat #715-007-003) as previously described (26). Appropriate FITC-, Cy3- or Cy5-conjugated secondary antibodies (1:1000; Jackson ImmunoResearch) in 2.5% NDS with 1×PBS were applied for 1-2 hour at RT, and coverslips were mounted onto Superfrost™ Plus coated glass slides (Fisher Scientific, cat #12-550-15) in Prolong Gold antifade media containing DAPI (Thermofisher; Cat #P36935). Stained coverslips were examined under epifluorescence using an inverted Zeiss AxioObserver D1 microscope using a Zeiss 40×/0.95 plan Apochromat air objective or a Zeiss 63×/1.4 plan Apochromat oil objective. Images were captured and analyzed using Zeiss ZEN software.

TABLE 1

Primary antibodies used in this study.

| Antigen | Host Species | Dilution | Manufacturer/ Catalogue # |
|---|---|---|---|
| ADP ribosylation factor 13B (ARL13B) | Rabbit | 1:3000 | Proteintech; Cat # 17711-1-AP |
| ADP ribosylation factor 13B (ARL13B) | Mouse | 1:3000 | Abcam; Cat# AB136648 |
| Orodigital facial syndrome 1 (OFD1) | Rabbit | 1:1000 | Novus; Cat#NBP189355 |
| Acetylated alpha Tubulin (aaTub) | Mouse | 1:3000 | Sigma; Cat# T6793 |
| Gamma-tubulin (gTub) | Mouse | 1:3000 | Sigma; Cat# T6557 |
| Inositol polyphosphate 5-phosphatase (INPP5E) | Rabbit | 1:1000 | Proteintech; Cat#17797-1-AP |
| Pericentriolar material 1 (PCM1) | Rabbit | 1:3000 | Bethyl; Cat# A301150A |
| Glial fibrillary acidic protein (GFAP) | Chicken | 1:5000 | Encor Biotechnology; Cat# CPCA-GFAP |
| Neuronal nuclei (NeuN) | Mouse | 1:2000 | Sigma; Cat# MAB377 |
| Pericentrin (Pcnt) | Mouse | 1:500 | BD Biosciences; Cat# 611815 |
| Pericentrin (Pcnt) | Rabbit | 1:2000 | Covance; Cat #: PRB-432C |
| Type 3 adenylyl cyclase (AC3) | Chicken | 1:5000 | Encor Biotechnology; Cat# CPCA-ACIII |
| Ki-67 | Chicken | 1:5000 | Encor Biotechnology; Cat# CPCA-Ki67 |
| Microtubule-associated proteins 1A/1B light chain 3B (LC3B) | Rabbit | 1:500 | Cell Signaling Technology; Cat# 3868s |
| phospho-AMPK (Thr172) | Rabbit | 1:1000 | Cell Signaling Technology; Cat# 2535s |

FIG. 1. Primary cilia on patient-derived gnome cells are ablated by TTFields. A) General approach to treat cells with a single or repeated exposure to TTFields in vitro. Cells that were grown adherent on glass coverslips had media supplemented with 10% fetal bovine serum (FBS). B-D) S7 control cells stained for OFD1 (red), which clusters around basal bodies/centrioles, and ARL13B (green) which enriches in the primary cilium. Nuclei are labeled with DAPI (blue). In control (B), ARL13B+ cilia (arrow in b1 zoom) from OFD1+ puncta (vertical line). In S7 TTFields-treated cells (C, D) ARl13B+ cilia appeared elongated (e.g. ci), detached or separated away from the OFD1+ basal body (e.g. d1) or somewhat dissolved or cloudy in appearance at OFD1 clusters (e.g. d2). OFD1 clusters in TTFields-treated cells appeared smaller/less intense compared to control (compare vertical lines between b1 and d1/d2). E) Control or 3 days of TTFields-treated L0 cells stained similar to B. Control cells display clear OFD1+ basal body (vertical line) at the base of ARL13B+ cilia (arrow). TTFields-treated cells displayed less intensely-labeled OFD1+ basal body (vertical line) with surrounding dispersed/cloudy puncta of ARL13B (arrow). F) Percent of ARL13B+ cilia in L0 cells in control vs TTFields. G) L0 (upper row) and S7 (bottom row) cells stained for ARL13B (green), acetylated alpha tubulin (aaTUB, red), and gamma-tubulin (gTUB, blue). Control cells show ARL13B+ cilia colocalized with aaTUB (arrow) with gTUB+ basal bodies (arrowheads). TTFields-treated cells have clustered/dispersed ARL13B signal with no clear aaTUB+ axoneme associated with the gTUB+ basal body. H) Percent of aaTUB+/ARL13B+ cilia in control or TTFields-treated L0 and S7 cells. *$p<0.001$, **$p<0.0001$(ANOVA) Scale bars (in μm)=10 (B) and 5 (G).

Figure 2:
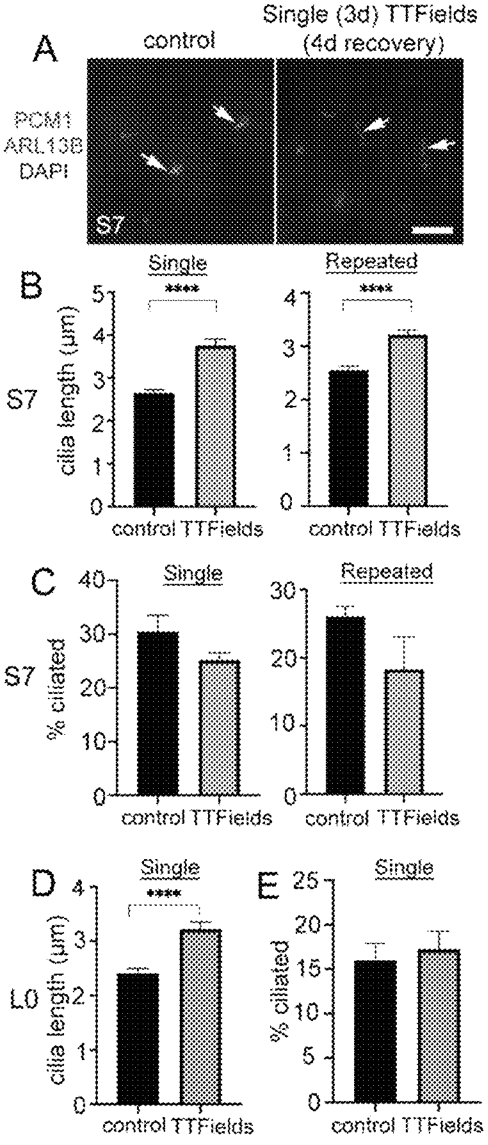
FIG. 2 shows similar frequencies of elongated glioma cilia after halting TTFields treatment.

FIG. 2. Similar frequencies of elongated glioma cilia after halting TTFields treatment. A) S7 cells with or without 3 days (3d) of TTFields treatment then dissociated onto coverslips for 4d. Fixed cells were immunostained for ARL13B (green) and PCM1 (red) with nuclei labeled with DAPI. Control and TTFields-treated cells showed ARL13B+ cilia (arrows) extending from PCM1+ puncta which concentrates around basal bodies. Scale bar=10 μm. B) Mean lengths of S7 ARL13B+ cilia after 4 days recovery from a single (left graph) or repeated (right graph) exposure to TTFields. C) Percent of ciliated cells after 4 days recovery from a single (left graph) or repeated (right graph) exposure to TTFields. D) Mean lengths of L0 ARL13B+ cilia after 4 days recovery from a single exposure to TTFields. E) Percent of ciliated L0 cells after 4 days recovery from a single exposure to TTFields.

Figure 3:
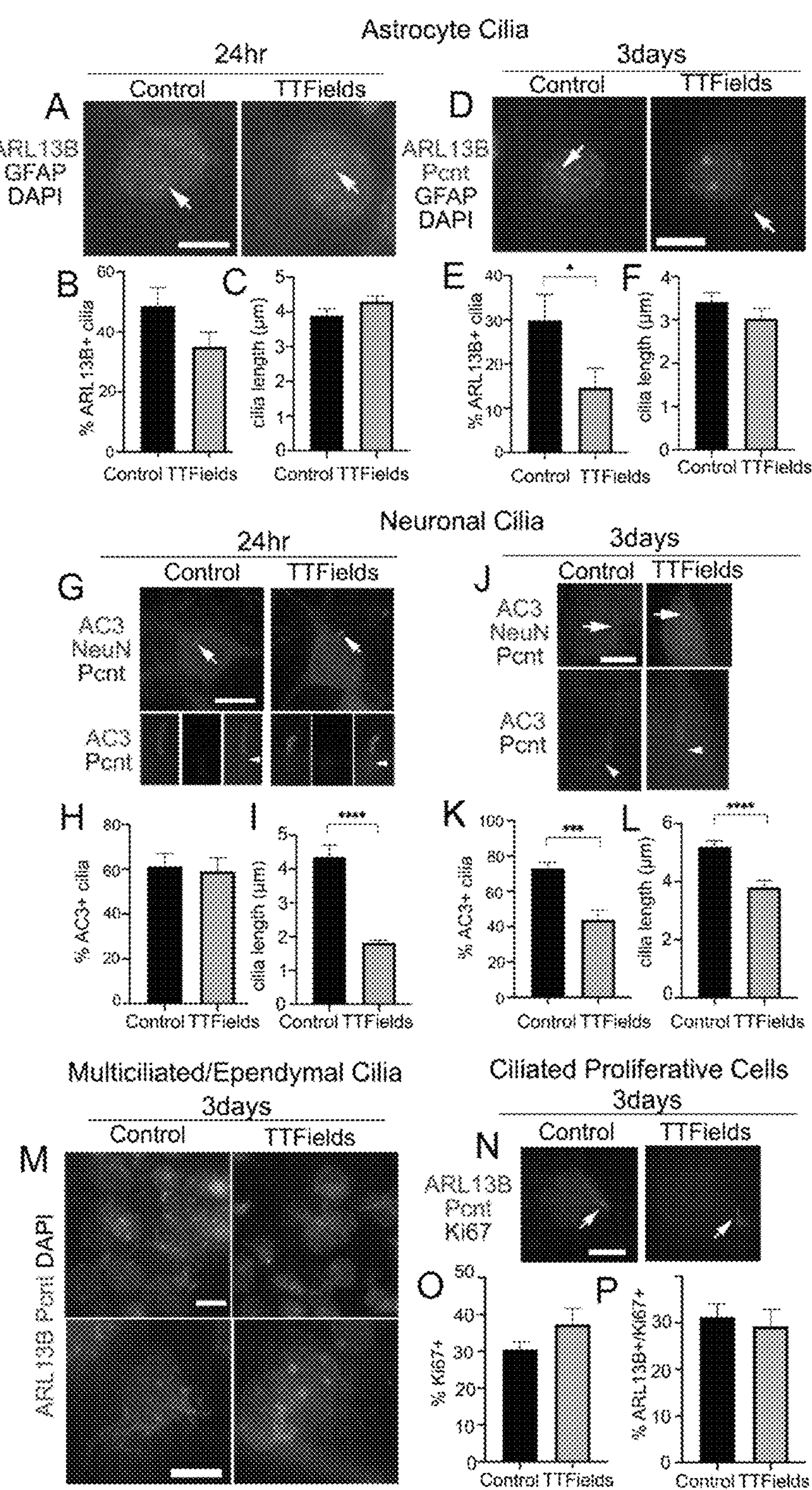
FIG. 3 shows effects of TTFields on normal mouse neural cell types in vitro.

FIG. 3. Effects of TTFields on normal mouse neural cell types in vitro. Mixed primary cultures from neonatal mouse cerebral cortex were dissociated and maintained for 11 DIV and left untreated (Control) or exposed to 24 hour or 3 days continuous TTFields and fixed. A) Cells were stained for ARL13B (green) and GFAP (blue) after 24-hour TTFields. Nuclei were labeld with DAPI. Arrows point to ARL13B+ cilia in both groups at 24 hours. B,C) Percent of GFAP+ cells with ARL13B+ cilia (B), and mean length of ARL13B+ cilia (C) on GFAP+ cells after 24 hours. D) Cells were stained for ARL13B (green), pericentrin (Pcnt, red), and GFAP (blue) after 3 days TTFields. E) Percent of GFAP+ cells with ARL13B+ cilia (E), and mean length of ARL13B+ cilia (F) on GFAP+ cells after 3 days. G) Cells were stained for type 3 adenylyl cyclase (AC3) (green), NeuN (red), and Pcnt (blue) after 24 hours TTFields. Nuclei were labeled with DAPI. The arrows in upper panels point to cilia enlarged below each image showing Pcnt+ basal bodies for indicated cilia. H, I) Percent of NeuN+ cells with AC3+ cilia (H), and mean length of ARL13B+ cilia (1) on NeuN+ cells after 24 hours TTFields. J) Cells were stained for AC3 (green), NeuN (red), and Pcnt (blue) after 3 days TTFields. The arrows in upper panels point to cilia enlarged below each image which shows the Pcnt+ basal bodies for indicated cilia. K, L) Percent of NeuN+ cells with AC3+ cilia (K), and mean length of ARL13B+ cilia (1) on NeuN+ cells after 3 days TTFields. M) Cells were stained with ARL13B (green) and Pcnt (red) with nuclei labeled with DAPI (white). Lower magnification (upper panels) and enlarged (lower panels) examples of multiciliated cells in control (left panels) and 3 days of TTFields (right panels). Bars=10 μm N) Cells were stained for ARL13B (green), Pcnt (red) and Ki67 (blue) after 3 days TTFields. Images show examples of Ki67+ nuclei with ARl13B+ cilia (arrows) extening from Pcnt+ basal bodies. 0) Percent of Ki67+ cells per field analyzed in each group. P) Percent Ki67+ cells with ARL13B+ cilia. *$p<0.05$, *$p<0.001$, **$p<0.0001$ (ANOVA).

Figure 4B:
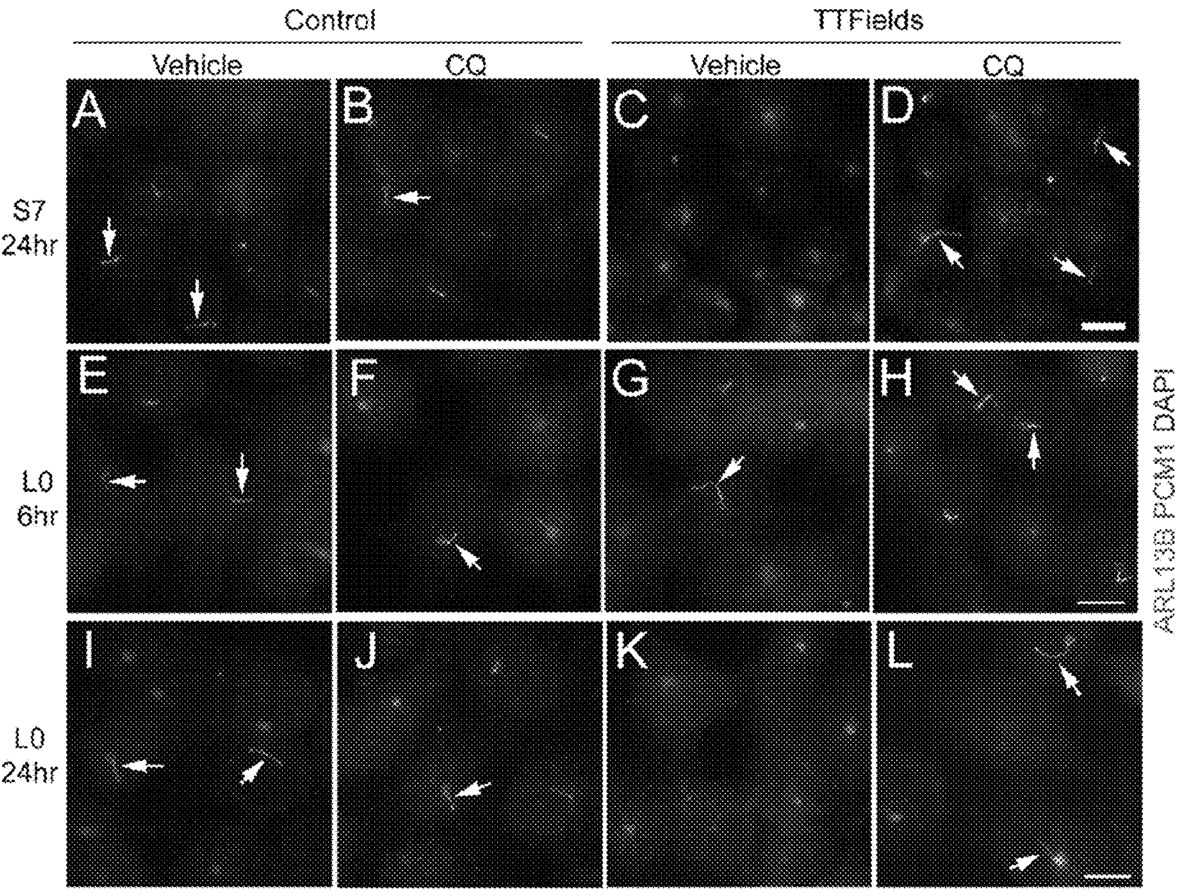

FIGS. 4*a* and 4*b*. Chloroquine pretreatment partially prevents TTFields-induced loss of cilia. In FIG. 4*a*, A-D) S7 cells pre-treated with vehicle (A, C) or 20 μM chloroquine (CQ) (B, D) and left untreated (control) (A,B) or exposed to 24 hours TTFields (C,D). Cells were stained for ARL13B (green), PCM1 (red) with nuclei stained with DAPI (blue). Arrows in (D) point to cilia observed in cells treated for 24 hours of CQ+ TTFields. Scale bar in D=10 μm. E, F) Percent of S7 (E) and L0 (F) cells with ARL13B+ cilia for the indicated treatment group after 6 hour (h) or 24 hours of TTFields (TTF). G,H) Mean lengths of ARL13B+ cilia in S7

(G) or L0 (H) cells for the indicated treatment group after 6 hours or 24 hours of TTFields (TTF). *p<0.05, p<0.01, *p<0.005, **p<0.0001(ANOVA). FIG. 4***b* provides additional immunostaining images reflected in the bar charts E, F, G, H in FIG. 4*a*: (A-D) 57 or (E-L) L0 cells pretreated with vehicle (A, C, E, G, I, K) or 20 μM chloroquine (Co) (B, F, J, D, H, L) and left untreated (control) (A, B, E, F, I, J) or exposed to TTFields (C,D, G, H, K, L). Cells were fixed after the indicated time point and stained for ARL13B (green) and PCM1 (red) with nuclei stained with DAPI (blue). Arrows point to cilia observed in the indicated treatments. Scale bars for the respective rows in (D, H, L)=10 μm.

FIGS. 5*a* and 5*b*. Temozolomide (TMZ) stimulates ciliogenesis in L0 and S7 cells. In FIG. 5*a*, A) S7 (left two columns) and L0 (right two columns) were grown for 24 hours in vehicle or 10 μM TMZ. Cells were fixed and immunostained for OFD1 (red), ARL13B (green). Nuclei were labeled with DAPI. TMZ-treated cells appeared to show elongated ARL13B+ cilia (arrowheads) and OFD1 intensity at the base of the cilia (arrows) appeared to decrease compared to vehicle in both cell lines. Scale bar=10 μm. B,C) Mean lengths of cilia in S7 (B) and L0 (C) cells after a 24 hours exposure to the indicated concentration [μM] of TMZ. D,F) Mean lengths of ARL13B+ cilia in S7 (D) or L0 (F) cells after a 3 day exposure to the indicated concentration [μM] of TMZ. E, G) Percent of ARL13B+ cilia in S7 (D) or L0 (F) cells after a 3-day exposure to the indicated concentration [μM] of TMZ. Figure Sb provides additional details: S7 (A) and L0 cells (B) were grown for 24 h in vehicle or 10 μM TMZ. Cells were fixed and immunostained for OFD1 (red) and ARL13B (green). Nuclei were labeled with DAPI. TMZ-treated cells appeared to show elongated ARL13B+ cilia (arrowheads) and OFD1 intensity at the base of the cilia (arrows) appeared to decrease compared with vehicle in both cell lines. Scale bar=10 μm. Mean lengths of cilia in (C) S7 and (D) L0 cells after a 24-h exposure to the indicated concentration (μM) of TMZ. (E) S7 and (F) L0 cells were grown for 72 h after one treatment of vehicle, 10 or 50 μM TMZ. Cells were fixed and immunostained for OFD1 (red) and ARL13B (green). Arrows point to ARL13B+ cilia in each treatment. Mean lengths of ARL13B+ cilia in (G) S7 or (1) L0 cells 3 days after exposure to the indicated concentration (μM) of TMZ. Percent of ARL13B+ cilia in (H) S7 or (J) L0 cells 3 days after exposure to the indicated concentration (μM) of TMZ. *p<0.05, p<0.01, *p<0.005, ****p<0.0001 (ANOVA).

FIG. 6. TTFields blocks the TMZ-mediated increase in ciliogenesis. A-D) Adherent S7 cells pre-treated with vehicle (A, C) or 10 μM TMZ (B, D) and left untreated (control) (A,B) or exposed to 3 days (d) TTFields (C,D). E-H) Adherent L0 cells pre-treated with vehicle (A, C) or 20 μM TMZ (B, D) and left untreated (control) (A,B) or exposed to 3 days TTFields. S7 and L0 cells were fixed and stained for ARL13B (green) and OFD1 (red). Nuclei are labeled with DAPI (blue). I-L) Spheres of S7 cells pre-treated with vehicle (I, K) or 50 μM TMZ (J, L) and left untreated (control) (IA or exposed to 3 days TTFields (K,L). To examine cilia, spheres were fixed, sectioned and stained for ARL13B (green, arrows). M, O) The number of cilia/per area ($\mu m^2$) of traced sections of S7 (M) or L0 (O) spheres for the indicated treatment. N, P) The mean length (μm) of cilia in S7 (N) or L0 (P) spheres for the indicated treatment. *p<0.05, p<0.01, *p<0.001, ****p<0.0001 (ANOVA). Scale bars (in μm) in A=10, 1=20.

FIGS. 7*a* and 7*b*. ARL13B+ cilia are linked to TMZ resistance and proliferation after TMZ and TTFields treatment. In FIG. 7*a*, A,B) Spheres of S7 parental or ARL13B KO (clone G12) cells were grown for 3 days and then treated with veh (vehicle), 50 or 100 μM TMZ and were exposed to an additional 3 days without (A) or with TTFields (B). Bar graphs in A,B show the normalized cell number (% of control) at the end of 6 days in the indicated group. C, D) S7 parental cells were treated with 100 μM TMZ for 3 days before a 24 hr treatment of TTFields or control (con). Cells were counted immediately after this treatment (C), and then pooled, and $2.5\times10^4$ cells/well were expanded in fresh media for 7 days in 24 well plates (n=12 wells/group). (D) Bar graph show the mean fold expansion per well for the indicated group. E,F) Similar experiment as (C,D) except TMZ was given for 3 days after a 24 hr TTFields treatment. G) Similar experiment as (E,F) but examining fold expansion of 57 ARL13B KO cells. ns=not significant, *p<0.05, p<0.01, *p<0.001, **p<0.0001 (ANOVA). FIG. 7***b* is an alternative presentation of the data: (A, B) S7 parental or ARL13B KO (clone G12) cells were grown as spheres for 4 days and then treated with vehicle (veh) or 50 or 100 μM TMZ and exposed to an additional 3 days without (A) or with TTFields. Bar graphs show the normalized cell number (% of control) at the end of 7 days. (C, D) TMZ "pre"-experiment: S7 parental cells were treated with 100 μM TMZ for 3 days before a 24-h treatment of TTFields or control (con). Cells were counted immediately after this treatment (acute count), and then pooled, and 2.5×104 cells/well were expanded in fresh media for 7 days in 24-well plates (n=12 wells/group), and the fold expansion was calculated (fold count) (D). (E, F) TMZ "post"-experiment: TMZ (100 μM) was given for 3 days after a 24-h TTFields treatment with S7 cells being counted acutely (E) or expanded in fresh media for 7 days (F). (G, H) TMZ "with" experiment: S7 cells were grown for 6 days and then simultaneously treated with TMZ (100 μM) and TTFields for 24 h, counted acutely (G) or examined for fold expansion after 7 days (H). (I) Similar experiment as (F) but examining fold expansion of S7 ARL13B KO cells after 6 days. n.d., not determined; ns, not significant; *p<0.05; p<0.01; *p<0.001; ****p<0.0001 (ANOVA).

Figure 8:
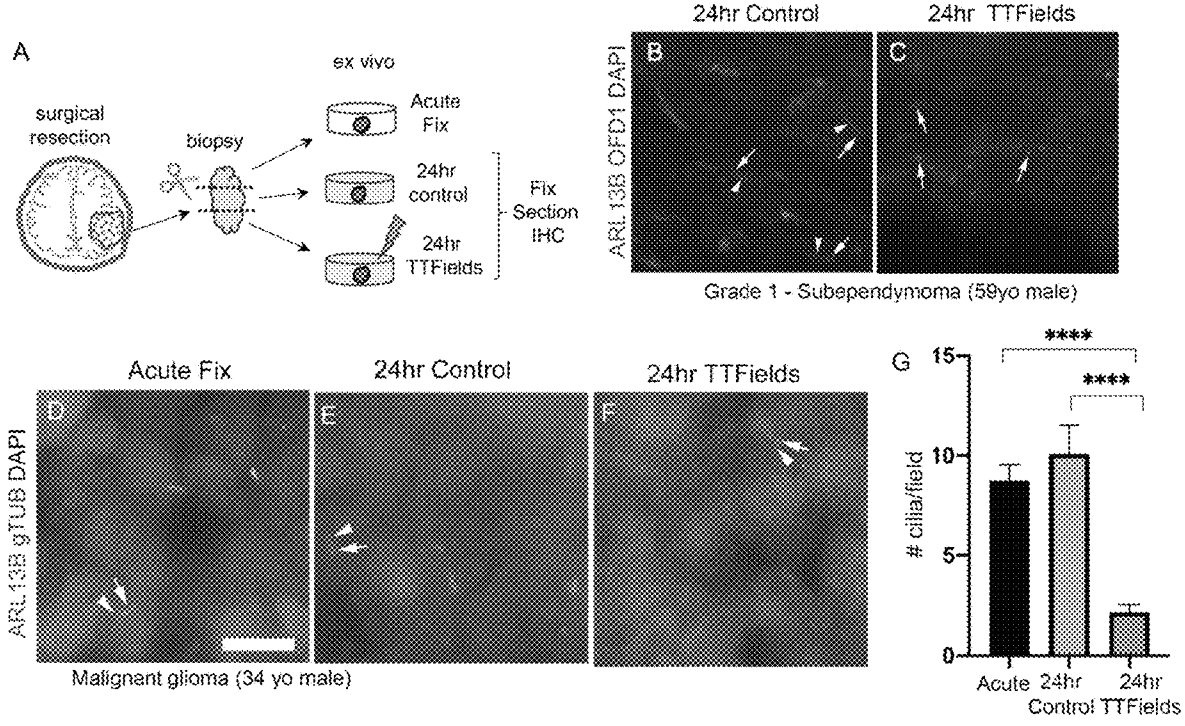
FIG. 8 shows TTFields disrupt cilia in patient samples ex-vivo.

FIG. 8. TTFields disrupt cilia in patient samples ex-vivo. A) Ex-vivo treatment of surgical resections. Biopsies were dissected and separated into immediate/acute fix, 24 hr control or 24 TTFields treatment. Tissue was fixed, frozen, cryosectioned and immunostained. Nuclei are labeled with DAPI. B) Immunostaining of control section of a Grade 1 subependymoma showed ARL13B+ cilia (arrowheads) extending from OFD1+ basal bodies (arrows). C) TTFields-treated tissue section showed OFD1+ basal bodies (arrows) without obvious ARL13B+ cilia extensions. D-F) Tissue from a malignant glioma from a 34-year-old male that was separated into immediate/acute fixation, 24 hour control, or 24 hour TTFields exposure. Tissues were fixed, cryosectioned and immunostained for ARL13B (green) and gTub (red), and nuclei labeled with DAPI (white). ARL13B+ cilia (arrows) with gTUB+ basal bodies (arrowheads) are readily detected in acute (D) and 24-hour control (E), but appeared blunted or generally absent in TTFields group (F). G) Mean (+/− SEM) number of cilia/field (n=12-13 fields/group) from samples in D-F. ****p<0.0001(ANOVA). Scale bars (in μm) in A=10.

Figure 9:
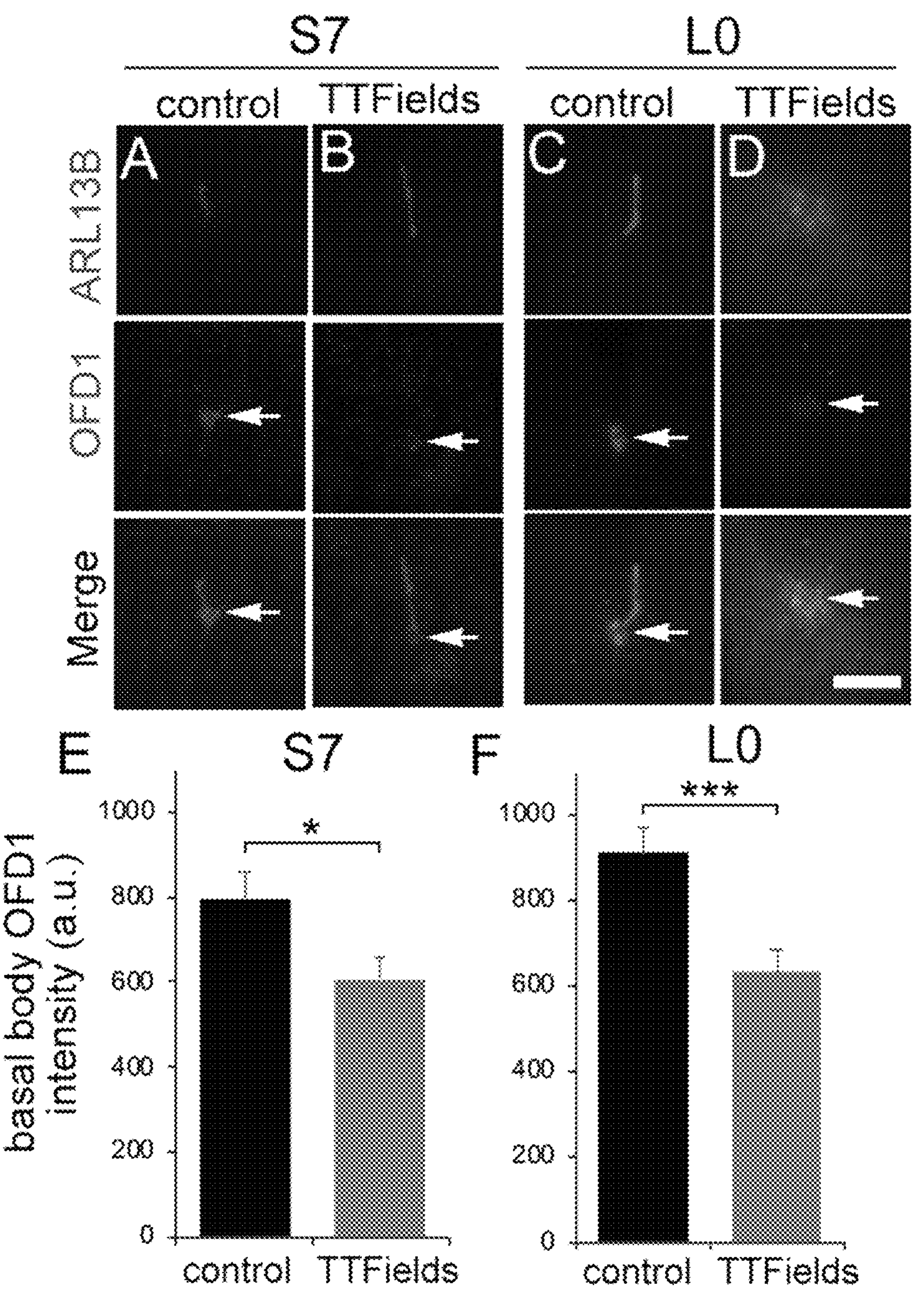
FIG. 9 shows reduced OFD1 expression around ciliary basal bodies/centrioles after TTFields.

FIG. 9. Reduced OFD1 expression around ciliary basal bodies/centrioles after TTFields. S7 and L0 cells were exposed to 3 days continuous TTFields. Cells were fixed in methanol and immunostained for ARL13B (green), and OFD1 (red). A-D) Example images of S7 control (A), S7 TTFields-treated (B), L0 control (C), and TTFields-treated (D). Immunostaining shows clusters of OFD1 (arrows) at the base of ARL13B' intact or dissolved cilia. E,F) Bar graphs show mean background-corrected fluorescence intensity of OFD1 between control or TTFields in S7 (E) and L0 (F) cells. a.u.=arbitrary units, *p<0.05, ***p<0.001 (ANOVA). Scale bar in D=5lim.

Figure 10:
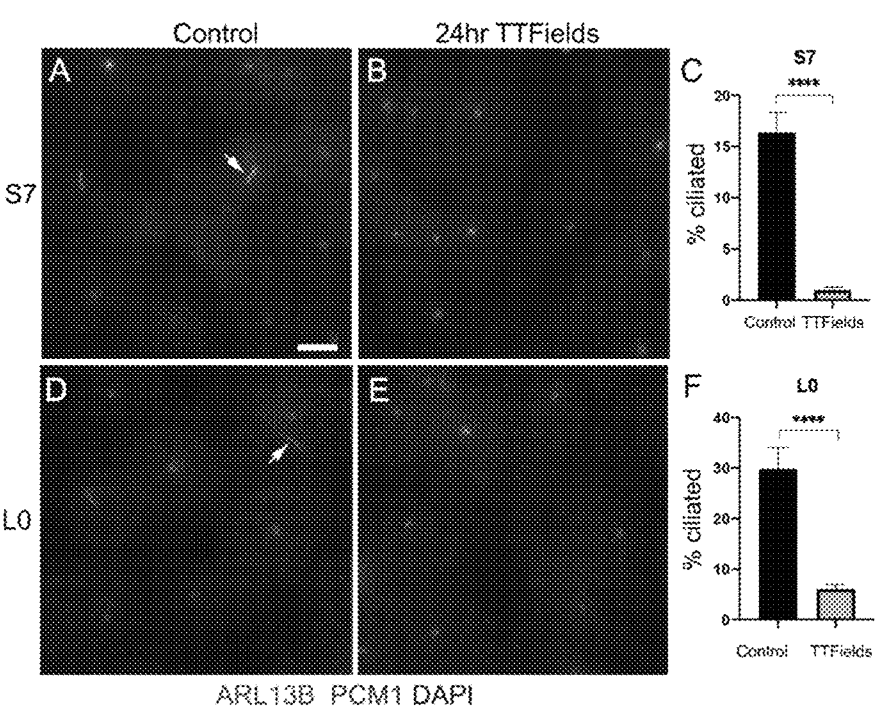
FIG. 10 shows applying TTFields ablates cilia within 24 hours in vitro.

FIG. 10. TTFields ablates cilia within 24 hours in vitro. A,B) S7 control (A) or TTFields-treated (B) cell stained for ARL13B (green), PCM1 (red). Nuclei are labeled with DAPI. C) Percentage of ARL13B+ cilia in S7 cells after 24 hours treatment. D,E) L0 control (D) or TTFields-treated (E) cell treated as in A,B. F) Percentage of ARL13B+ ciliated L0 cells after 24 hour treatment. ****p<0.0001(ANOVA) Scale bars (in μm) in A=10.

Figure 11:
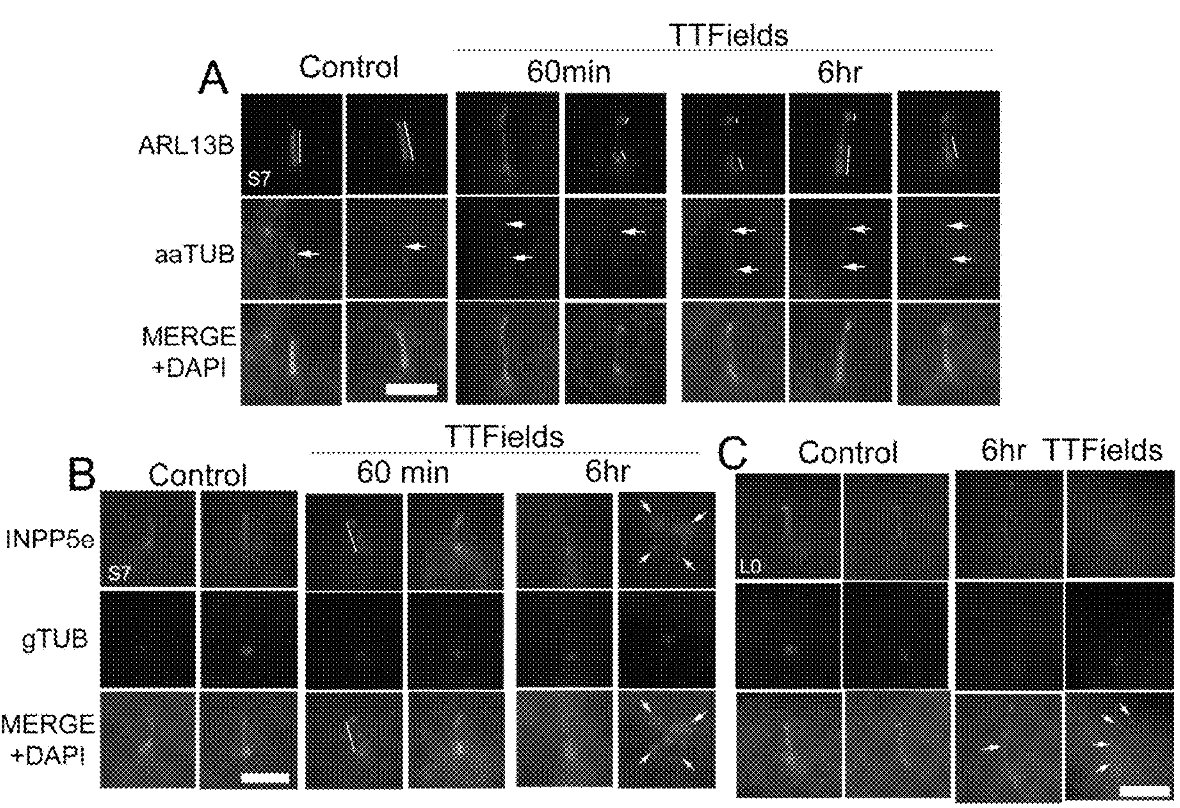
FIG. 11 shows cilia elongation and alteration of ciliary membrane proteins by 6 hours of TTFields.

FIG. 11. Cilia elongation and alteration of ciliary membrane proteins by 6 hours of TTFields. A) Adherent S7 control or TTFields-treated (60 min or 6 hours) cells were fixed and immunostained for ARL13B (red) and aaTUB (green). In control, the distribution of ARL13B was relatively even along the length of the cilium (vertical lines). In TTFields exposed cells, the ARL13B distribution appears to polarize towards the base and distal tip. By 6 hours, TTFields cilia appeared longer with detectable underlying aaTUB+ axonemes (arrows). B) Similar experiment as A, except we immunostained for INPPSe (green) which localizes to cilia membrane, and gamma-tubulin (gTUB, red) which is a component of the basal body/centriole. Like ARL13B, INPPSe distribution was largely evenly distributed along the length of the cilium but appeared puncta or polarized after TTFields. After 6 hours TTFields we also observed abnormal clusters of INNPSe (arrows) surrounding the gTUB+ basal body/centriole. C) Adherent L0 control or TTFields treated cells stained for INPPSe and gTUB. TTFields-treated L0 cilia were also long and showed abnormal INNPSe distribution along the cilium. Scale bars in A, B and C=5 μm.

Figure 12:
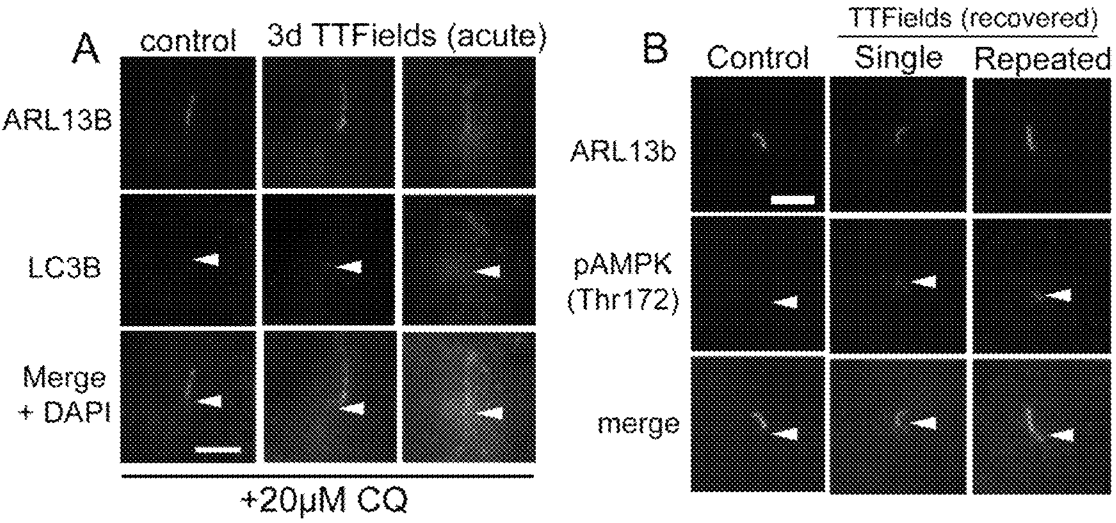
FIG. 12 shows autophagy components LC3B and pAMPK localize to cilia after TTFields.

FIG. 12. Autophagy components LC3B and pAMPK localize to cilia after TTFields. A) S7 control or TTFields-treated cells had 20 μM chloroquine (CQ) added 3 hours before halting treatment and fixing cells. Cells were fixed and immunostained for ARL13B (green) and LC3B (red). TTFields treated cells showed recruitment or clustering of LC3B particles around the cilia/cilia base (arrowheads) compared to control. B) S7 control or TTFields-treated cells (either single 3-day continuous exposure) or repeated 3 days (as described in FIG. 1A). Cells recovered for 4 days and were fixed and immunostained for pAMPK (Thr172), red). pAMPK signal was detected at the base of TTFields treated cilia compared to control (arrowheads). Scale bars in A and B=5 μm.

Figure 13:
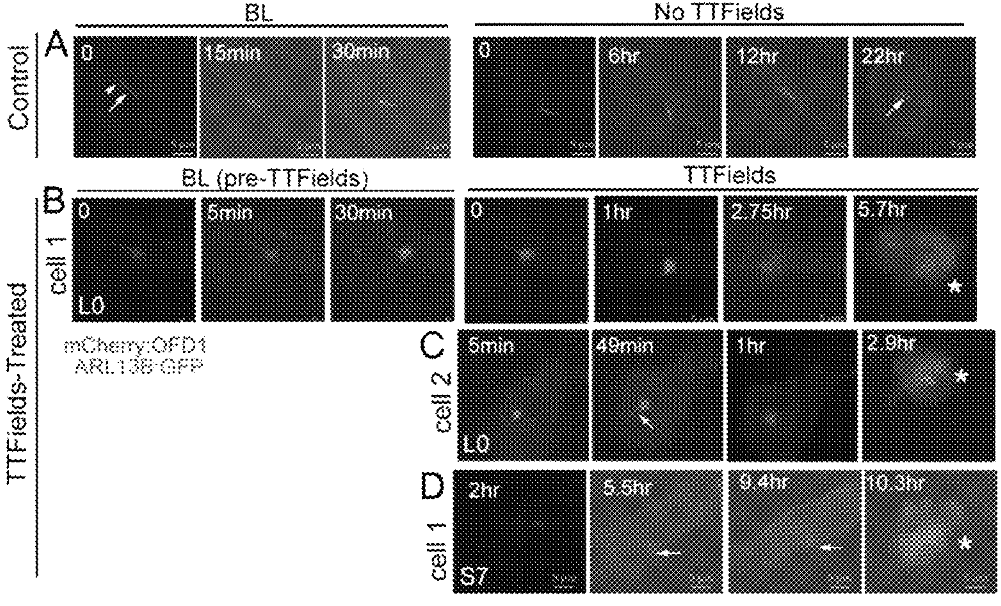
FIG. 13 shows live imaging of glioma cilia during TTFields reveals death of ciliated cells.

FIG. 13. Live imaging of glioma cilia during TTFields reveals death of ciliated cells. A) Time-lapse imaging of glioma cell transfected 24 hr prior to imaging with cDNA encoding mCherry-tagged OFD1 (red) and GFP-tagged ARL13b (green) using lipofectamine. mCherry-OFD1 clusters around the basal body (arrowhead) whereas Ar113b: GFP enriches in the cilium (arrow). The row of images shows the cilium at indicated timepoints during baseline (BL) (images taken every minute) or overnight (images captured every 5 min) recording. B) Example of an L0 cilium during BL and TTFields. At 5.7 hr the cell appears to die (asterisk). C) Another example of an L0 cell that appears to die during TTFields. D) Example of a ciliated S7 cell (e.g arrow at 5.5 hr) in which the cilium is not clearly visible at 9.4 hr and the cell appears to die by 10.3 during TTFields. Bar=5 μm for all time lapse images.

FIG. 14. Loss of cilia in a glioblastoma biopsy treated with TTFields ex vivo. A-C) Fresh surgical resection from a glioblastoma from a 66-year-old male was separated into immediate/acute fixation, 24-hour control, or 24 hour TTFields exposure. Tissues were fixed, cryosectioned and immunostained for ARL13B (green) and gTub (red), and nuclei labeled with DAPI (blue). ARL13B+ cilia (arrows) with gTUB+ basal bodies (arrowheads) are readily detected in acute (A) and 24-hour control (B), blunted or generally absent in TTFields group (C).

Alternating electric fields (AEFs), also known as Tumor Treating Fields (TTFields), are low voltage, alternating high frequency (200 kHz) electrical fields that extend survival of malignant glioma patients when combined with temozolomide (TMZ) chemotherapy. How TTFields exerts efficacy over normal cells, or interacts with TMZ is unclear. Primary cilia are microtubule-based organelles triggered by extracellular ligands, mechanical and electrical field stimulation, and capable of promoting cancer growth and TMZ chemoresistance. We found in both low and high grade patient glioma cell lines that TTFields ablated cilia within 24 hours. Halting TTFields treatment led to recovered frequencies of elongated cilia. Cilia on normal primary astrocytes, neurons, and multiciliated/ependymal cells were less affected by TTFields. The TTFields-mediated loss of glioma cilia was partially rescued by chloroquine pretreatment, suggesting the effect is in part due to autophagy activation. We also directly observed death of ciliated cells during TTFields by live imaging. Notably, TMZ-induced stimulation of ciliogenesis in both adherent glioma cells and gliomaspheres was blocked by TTFields. Moreover, combining TMZ and TTFields slowed tumor cell recurrence of ARL13B+ ciliated but not ARL13B-non-ciliated tumor cells. Finally, we show that TTFields disrupt cilia in patient tumors treated ex vivo. Our findings indicate that TTFields may have a greater impact on tumors with enhanced ciliogenesis to promote TMZ sensitivity.

Certain non-limiting aspects of the present disclosure are directed to methods of determining susceptibility of cancer cells of a subject to treatment with alternating electric fields. Such methods including applying alternating electric fields to a first batch of cancer cells obtained or derived from a subject; ascertaining, after applying the alternating electric fields to the first batch, a first percentage of the cancer cells of the first batch that are ciliated; ascertaining a second percentage of a second batch of cancer cells obtained or derived from the subject that are ciliated, wherein the second batch was not exposed to alternating electric fields prior to ascertaining the second percentage; and determining that the cancer cells of the subject are susceptible to treatment with alternating electric fields if the first percentage is lower than the second percentage.

Certain additional non-limiting aspects of the present disclosure are directed to methods of reducing the viability of cancer cells of a subject, by applying alternating electric fields to a first batch of cancer cells obtained or derived from a subject; ascertaining, after applying the alternating electric fields to the first batch, a first percentage of the cancer cells of the first batch that are ciliated; ascertaining a second percentage of a second batch of cancer cells obtained or derived from the subject that are ciliated, wherein the second batch was not exposed to alternating electric fields prior to ascertaining the second percentage; and applying alternating electric fields to the cancer cells if the first percentage is lower than the second percentage.

In an aspect, the determining includes determining that the cancer cells of the subject are susceptible to treatment with alternating electric fields if the percentage of the cancer cells of the first batch that are ciliated is at least 20% lower than the percentage of the cancer cells of the second batch that are ciliated, for example, at least 25% lower, at least 30% lower, at least 35% lower, or at least 40% lower. In an aspect, the determining includes determining that the cancer cells of the subject are susceptible to treatment with alternating electric fields if the percentage of the cancer cells of the first batch that are ciliated is at least 15% lower than the percentage of the cancer cells of the second batch that are ciliated.

In an aspect, the percentages of the cancer cells that are ciliated are ascertained by imaging cancer cells. In particular, cancer cells can be imaged by confocal microscopy or light microscopy or RT-PCR. In another aspect, the percentages of the cancer cells that are ciliated are ascertained by determining a level of ARL13B or of OTD1 in the first batch and the second batch.

Certain additional non-limiting aspects of the present disclosure provide methods of determining susceptibility of cancer cells of a subject to treatment with alternating electric fields, including applying alternating electric fields to a first batch of cancer cells obtained or derived from a subject; ascertaining, after applying the alternating electric fields to the first batch, an average length of a primary cilia of cancer cells of the first batch; ascertaining an average length of a primary cilia of cancer cells of the second batch; and determining that the cancer cells of the subject are susceptible to treatment with alternating electric fields if the average length of the primary cilia of the first batch is shorter than the average length of the primary cilia of the second batch.

Certain additional non-limiting aspects of the present disclosure provide methods of reducing the viability of cancer cells of a subject, including: applying alternating electric fields to a first batch of cancer cells obtained or derived from a subject; ascertaining, after applying the alternating electric fields to the first batch, an average length of a primary cilia of cancer cells of the first batch; ascertaining an average length of a primary cilia of cancer cells of the second batch; and applying alternating electric fields to the cancer cells in the subject if the average length of the primary cilia of the first batch is shorter than the average length of the primary cilia of the second batch.

In an aspect, the determining includes determining that the cancer cells of the subject are susceptible to treatment with alternating electric fields if the average length of the primary cilia of the first batch is at least 20% shorter than the average length of the primary cilia of the second batch, for example, at least 25% shorter, at least 30% shorter, at least 35% shorter, or at least 40% shorter. In an aspect, the determining includes determining that the cancer cells of the subject are susceptible to treatment with alternating electric fields if the average length of the primary cilia of the first batch is at least 20% shorter than the average length of the primary cilia of the second batch.

In an aspect, the average length of the primary cilia is ascertained by imaging cancer cells. In an aspect, the average length of the primary cilia is ascertained by confocal microscopy or light microscopy.

Any type of conductive or non-conductive electrode(s) and/or transducer array(s) that can be utilized for generating an alternating electric field that are known in the art or otherwise contemplated herein may be utilized for generation of the alternating electric field in accordance with the methods of the present disclosure. Non-limiting examples of electrodes and transducer arrays that can be utilized for generating an alternating electric field in accordance with the present disclosure include those that function as part of a TTFields system as described, for example but not by way of limitation, in U.S. Pat. Nos. 7,016,725; 7,089,054; 7,333,852; 7,565,205; 8,244,345; 8,715,203; 8,764,675; 10,188,851; and 10,441,776; and in US Patent Application Nos. US 2018/0160933; US 2019/0117956; US 2019/0307781; and US 2019/0308016.

The alternating electric field may be generated at any frequency in accordance with the present disclosure. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, about 500 kHz, about 550 kHz, about 600 kHz, about 650 kHz, about 700 kHz, about 750 kHz, about 800 kHz, about 850 kHz, about 900 kHz, about 950 kHz, about 1 MHz, about 2 MHz, about 3 MHz, about 4 MHz, about 5 MHz, about 6 MHz, about 7 MHz, about 8 MHz, about 9 MHz, about 10 MHz, and the like, as well as a range formed from any of the above values (e.g., a range of from about 50 kHz to about 10 MHz, a range of from about 50 kHz to about 1 MHz, a range of from about 50 kHz to about 500 kHz, a range of from about 100 kHz to about 500 kHz, a range of from about 150 kHz to about 300 kHz, etc.), and a range that combines two integers that fall between two of the above-referenced values (e.g., a range of from about 122 kHz to about 313 kHz, a range of from about 78 kHz to about 298 kHz, etc.).

In certain particular (but non-limiting) embodiments, the alternating electric field may be imposed at two or more different frequencies. When two or more frequencies are present, each frequency is selected from any of the above-referenced values, or a range formed from any of the above-referenced values, or a range that combines two integers that fall between two of the above-referenced values.

The alternating electric field may have any field strength in the subject/cancer cells, so long as the alternating electric field is capable of functioning in accordance with the present disclosure. For example (but not by way of limitation), the alternating electric field may have a field strength of at least about 1 V/cm, about 1.5 V/cm, about 2 V/cm, about 2.5 V/cm, about 3 V/cm, about 3.5 V/cm, about 4 V/cm, about 4.5 V/cm, about 5 V/cm, about 5.5 V/cm, about 6 V/cm, about 6.5 V/cm, about 7 V/cm, about 7.5 V/cm, about 8 V/cm, about 9 V/cm, about 9.5 V/cm, about 10 V/cm, about 10.5 V/cm, about 11 V/cm, about 11.5 V/cm, about 12 V/cm, about 12.5 V/cm, about 13 V/cm, about 13.5 V/cm, about 14 V/cm, about 14.5 V/cm, about 15 V/cm, about 15.5 V/cm, about 16 V/cm, about 16.5 V/cm, about 17 V/cm, about 17.5 V/cm, about 18 V/cm, about 18.5 V/cm, about 19 V/cm, about 19.5 V/cm, about 20 V/cm, and the like, as well as a range formed from any of the above values (e.g., a range of from about 1 V/cm to about 20 V/cm, a range of from about 1 V/cm to about 10 V/cm, a range of from about 1 V/cm to about 4 V/cm, etc.), and a range that combines two integers that fall between two of the above-referenced values (e.g., a range of from about 1.1 V/cm to about 18.6 V/cm, a range of from about 1.2 V/cm to about 9.8 V/cm, a range of from about 1.3 V/cm to about 4.7 V/cm, etc.).

The alternating electric field may be applied for any period of time sufficient to achieve a reduction in viability of cancer cells and/or a reduction in tumor volume (and/or a prevention of increase in tumor volume). For example, but not by way of limitation, the alternating electric field may be applied for at least about 1 hour, about 2 hours, about 3 hours, about 4 hours, about 5 hours, about 6 hours, about 7 hours, about 8 hours, about 9 hours, about 10 hours, about 11 hours, about 12 hours, about 15 hours, about 18 hours, about 21 hours, about 24 hours, about 27 hours, about 30 hours, about 33 hours, about 36 hours, about 39 hours, about 42 hours, about 45 hours, about 48 hours, about 51 hours, about 54 hours, about S7 hours, about 60 hours, about 63 hours, about 66 hours, about 69 hours, about 72 hours, about 75 hours, about 78 hours, about 81 hours, about 84 hours, about 87 hours, about 90 hours, about 93 hours, about 96 hours, about 5 days, about 6 days, about 7 days, and the like, as well as a range formed from any of the above values (e.g., a range of from about 24 hours to about 72 hours, etc.), and a range that combines two integers that fall between two of the above-referenced values (e.g., a range of from about 14 hours to about 68 hours, etc.).

In a particular (but non-limiting) embodiment, the period of time that the alternating electric field is applied is at least about 24 hours.

In certain aspects, the method further includes administering a chemotherapeutic agent to the cancer cells in the subject. Non-limiting examples of chemotherapeutic agents that can be utilized in accordance with the present disclosure include anti-PD-1 therapeutics such as (but not limited to) Pembrolizumab, Tislelizumab, Nivolumab, and Cemiplimab; anti-PD-L1 therapeutics such as atezolizumab, avelumab, and durvalumab; chemotherapeutic agents, such as (but not limited to); Paclitaxel, Docetaxel, Ifosamide, Etoposide (Vepesid), Gemcitabine, Lomustine, nab Paclitaxel, temozolomide (TMZ), and Carboplatin; TKI inhibitors, such as (but not limited to) Everolimus; mTOR inhibitors; Akt inhibitors; PI3K inhibitors; PARP inhibitors; anti-CTLA-4 therapeutics. In certain aspects the chemotherapeutic agent is TMZ.

The methods of the present disclosure may be utilized to treat any types of cancer cells/cancers/tumors. Non-limiting examples of cancer cells/cancers/tumors that can be treated in accordance with the present disclosure include hepatocellular carcinomas, glioblastomas, pleural mesotheliomas, differentiated thyroid cancers, advanced renal cell carcinomas, ovarian cancers, pancreatic cancers, lung cancers, breast cancers, and the like, as well as any combination thereof.

Huntington's Disease

The methods of the present disclosure may be utilized to treat Huntington's disease in a subject in need of such treatment. Such patients may have been diagnosed as having Huntington's disease. Huntington's disease is a dominant autosomal disorder of nerve cells that is deprived of treatment options. Disease onset affects the brain, manifesting in uncontrolled movement of the body but also in depression and decline in thinking and reasoning. It has been previously described as a disease of nerve cells with morphology of uncontrolled hypermorphic ciliogenesis and ciliary dysfunction leading to a change in molecular signaling of cells indicating that increased ciliogenesis may affect neuronal survival. Without being bound by theory, application of an alternating electric field as described herein may be used to treat Huntington's disease by treating the underlying ciliogenesis of neurons.

In an aspect, the disclosure provides a method of treating Huntington's disease in a subject in need of treatment, by applying an alternating electric field to a brain of the subject. For example, a method may include applying an alternating electric field to a neuron (nerve cell) in a brain of the subject. In some aspects the patient is cancer-free. In some aspects the patient has not been diagnosed with glioblastoma. In some aspects the patient has not been diagnosed with cancer.

Any type of conductive or non-conductive electrode(s) and/or transducer array(s) that can be utilized for generating an alternating electric field that are known in the art or otherwise contemplated herein may be utilized for generation of the alternating electric field in accordance with the methods of the present disclosure. Non-limiting examples of electrodes and transducer arrays that can be utilized for generating an alternating electric field in accordance with the present disclosure include those that function as part of a TTFields system as described, for example but not by way of limitation, in U.S. Pat. Nos. 7,016,725; 7,089,054; 7,333,852; 7,565,205; 8,244,345; 8,715,203; 8,764,675; 10,188,851; and 10,441,776; and in US Patent Application Nos. US 2018/0160933; US 2019/0117956; US 2019/0307781; and US 2019/0308016.

The alternating electric field may be generated at any frequency in accordance with the present disclosure. For example (but not by way of limitation), the alternating electric field may have a frequency of about 50 kHz, about 75 kHz, about 100 kHz, about 125 kHz, about 150 kHz, about 175 kHz, about 200 kHz, about 225 kHz, about 250 kHz, about 275 kHz, about 300 kHz, about 325 kHz, about 350 kHz, about 375 kHz, about 400 kHz, about 425 kHz, about 450 kHz, about 475 kHz, about 500 kHz, about 550 kHz, about 600 kHz, about 650 kHz, about 700 kHz, about 750 kHz, about 800 kHz, about 850 kHz, about 900 kHz, about 950 kHz, about 1 MHz, about 2 MHz, about 3 MHz, about 4 MHz, about 5 MHz, about 6 MHz, about 7 MHz, about 8 MHz, about 9 MHz, about 10 MHz, and the like, as well as a range formed from any of the above values (e.g., a range of from about 50 kHz to about 10 MHz, a range of from about 50 kHz to about 1 MHz, a range of from about 50 kHz to about 500 kHz, a range of from about 100 kHz to about 500 kHz, a range of from about 150 kHz to about 300 kHz, etc.), and a range that combines two integers that fall between two of the above-referenced values (e.g., a range of from about 122 kHz to about 313 kHz, a range of from about 78 kHz to about 298 kHz, etc.).

In certain particular (but non-limiting) embodiments, the alternating electric field may be imposed at two or more different frequencies. When two or more frequencies are present, each frequency is selected from any of the above-referenced values, or a range formed from any of the above-referenced values, or a range that combines two integers that fall between two of the above-referenced values.

The alternating electric field may have any field strength in the brain/nerve cells, so long as the alternating electric field is capable of functioning in accordance with the present disclosure. For example (but not by way of limitation), the alternating electric field may have a field strength of at least about 1 V/cm, about 1.5 V/cm, about 2 V/cm, about 2.5 V/cm, about 3 V/cm, about 3.5 V/cm, about 4 V/cm, about 4.5 V/cm, about 5 V/cm, about 5.5 V/cm, about 6 V/cm, about 6.5 V/cm, about 7 V/cm, about 7.5 V/cm, about 8 V/cm, about 9 V/cm, about 9.5 V/cm, about 10 V/cm, about 10.5 V/cm, about 11 V/cm, about 11.5 V/cm, about 12 V/cm, about 12.5 V/cm, about 13 V/cm, about 13.5 V/cm, about 14 V/cm, about 14.5 V/cm, about 15 V/cm, about 15.5 V/cm, about 16 V/cm, about 16.5 V/cm, about 17 V/cm, about 17.5 V/cm, about 18 V/cm, about 18.5 V/cm, about 19 V/cm, about 19.5 V/cm, about 20 V/cm, and the like, as well as a range formed from any of the above values (e.g., a range of from about 1 V/cm to about 20 V/cm, a range of from about 1 V/cm to about 10 V/cm, a range of from about 1 V/cm to about 4 V/cm, etc.), and a range that combines two integers that fall between two of the above-referenced values (e.g., a range of from about 1.1 V/cm to about 18.6 V/cm, a range of from about 1.2 V/cm to about 9.8 V/cm, a range of from about 1.3 V/cm to about 4.7 V/cm, etc.).

The alternating electric field may be applied for any period of time sufficient to achieve a reduction in degree of ciliation of nerve cells and/or a reduction average length of a primary cilia of a nerve cell. For example, but not by way of limitation, the alternating electric field may be applied for at least about 1 hour, about 2 hours, about 3 hours, about 4 hours, about 5 hours, about 6 hours, about 7 hours, about 8 hours, about 9 hours, about 10 hours, about 11 hours, about 12 hours, about 15 hours, about 18 hours, about 21 hours, about 24 hours, about 27 hours, about 30 hours, about 33 hours, about 36 hours, about 39 hours, about 42 hours, about 45 hours, about 48 hours, about 51 hours, about 54 hours, about S7 hours, about 60 hours, about 63 hours, about 66 hours, about 69 hours, about 72 hours, about 75 hours, about 78 hours, about 81 hours, about 84 hours, about 87 hours, about 90 hours, about 93 hours, about 96 hours, about 5 days, about 6 days, about 7 days, and the like, as well as a range formed from any of the above values (e.g., a range of from about 24 hours to about 72 hours, etc.), and a range that combines two integers that fall between two of the above-referenced values (e.g., a range of from about 14 hours to about 68 hours, etc.).

In a particular (but non-limiting) embodiment, the period of time that the alternating electric field is applied is at least about 12 hours. In a particular (but non-limiting) embodiment, the period of time that the alternating electric field is applied is at least about 24 hours.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

REFERENCES

1. Stupp R, Hegi M E, Mason W P, van den Bent M J, Taphoorn M J, Janzer R C, et al. Effects of radiotherapy with concomitant and adjuvant temozolomide versus radiotherapy alone on survival in glioblastoma in a randomised phase III study: 5-year analysis of the EORTC-NCIC trial. *Lancet Oncol.* 2009; 10(5):459-66.
2. Stupp R, Mason W P, van den Bent M J, Weller M, Fisher B, Taphoorn M J, et al. Radiotherapy plus concomitant and adjuvant temozolomide for glioblastoma. *N Engl J Med.* 2005; 352(10):987-96.
3. Stupp R, Taillibert 5, Kanner A, Read W, Steinberg D M, Lhermitte B, et al. Effect of Tumor-Treating Fields Plus Maintenance Temozolomide vs Maintenance Temozolomide Alone on Survival in Patients With Glioblastoma: A Randomized Clinical Trial. *JAMA.* 2017; 318(23):2306-16.
4. Stupp R, Taillibert 5, Kanner A A, Kesari 5, Steinberg D M, Toms S A, et al. Maintenance Therapy With Tumor-Treating Fields Plus Temozolomide vs Temozolomide Alone for Glioblastoma: A Randomized Clinical Trial. *JAMA.* 2015; 314(23):2535-43.
5. Mehta M, Wen P, Nishikawa R, Reardon D, and Peters K. Critical review of the addition of tumor treating fields (TTFields) to the existing standard of care for newly diagnosed glioblastoma patients. *Crit Rev Oncol Hematol.* 2017; 111:60-5.
6. Karanam N K, and Story M D. An overview of potential novel mechanisms of action underlying Tumor Treating Fields-induced cancer cell death and their clinical implications. Intl Radiat Biol. 2021; 97(8):1044-54.
7. Kirson E D, Gurvich Z, Schneiderman R, Dekel E, Itzhaki A, Wasserman Y, et al. Disruption of cancer cell replication by alternating electric fields. *Cancer Res.* 2004; 64(9):3288-95.
8. Kirson E D, Dbaly V, Tovarys F, Vymazal 1, Soustiel J F, Itzhaki A, et al. Alternating electric fields arrest cell proliferation in animal tumor models and human brain tumors. *Proc Natl Acad Sci USA.* 2007; 104(24):10152-7.
9. Giladi M, Schneiderman R S, Voloshin T, Porat Y, Munster M, Blat R, et al. Mitotic Spindle Disruption by Alternating Electric Fields Leads to Improper Chromosome Segregation and Mitotic Catastrophe in Cancer Cells. *Sci Rep.* 2015; 5:18046.
10. Kim E H, Song H S, Yoo S H, and Yoon M. Tumor treating fields inhibit glioblastoma cell migration, invasion and angiogenesis. Oncotarget. 2016; 7(40):65125-36.
11. Silginer M, Weller M, Stupp R, and Roth P. Biological activity of tumor-treating fields in preclinical glioma models. *Cell Death Dis.* 2017; 8(4):e2753.
12. Schneiderman R S, Shmueli E, Kirson E D, and Palti Y. TTFields alone and in combination with chemotherapeutic agents effectively reduce the viability of MDR cell sub-lines that over-express ABC transporters. *BMC Cancer.* 2010; 10:229.
13. Kessler A F, Frombling G E, Gross F, Hahn M, Dzokou W, Ernestus R I, et al. Effects of tumor treating fields (TTFields) on glioblastoma cells are augmented by mitotic checkpoint inhibition. *Cell Death Discov.* 2018; 4:12.
14. Shteingauz A, Porat Y, Voloshin T, Schneiderman R S, Munster M, Zeevi E, et al. AMPK-dependent autophagy upregulation serves as a survival mechanism in response to Tumor Treating Fields (TTFields). *Cell Death Dis.* 2018; 9(11):1074.
15. Voloshin T, Kaynan N, Davidi 5, Porat Y, Shteingauz A, Schneiderman R S, et al. Tumor-treating fields (TTFields) induce immunogenic cell death resulting in enhanced antitumor efficacy when combined with anti-PD-1 therapy. *Cancer Immunol Immunother.* 2020; 69(7):1191-204.
16. Chang E, Patel C B, Pohling C, Young C, Song J, Flores T A, et al. Tumor treating fields increases membrane permeability in glioblastoma cells. *Cell Death Discov.* 2018; 4:113.
17. Neuhaus E, Zirjacks L, Ganser K, Klumpp L, Schuler U, Zips D, et al. Alternating Electric Fields (TTFields) Activate Cav1.2 Channels in Human Glioblastoma Cells. Cancers (Basel). 2019; 11(1).
18. Goetz S C, and Anderson K V. The primary cilium: a signalling centre during vertebrate development. *Nat Rev Genet.* 2010; 11(5):331-44.
19. Wheway G, Nazlamova L, and Hancock J T. Signaling through the Primary Cilium. Front Cell *Dev Biol.* 2018; 6:8.
20. Reiter J F, and Leroux M R. Genes and molecular pathways underpinning ciliopathies. Nature reviews. 2017; 18(9):533-47.

21. Garcia G, 3rd, Raleigh D R, and Reiter J F. How the Ciliary Membrane Is Organized Inside-Out to Communicate Outside-In. *Curr Biol.* 2018; 28(8):R421-R34.

22. Garcia-Gonzalo F R, Phua S C, Roberson E C, Garcia G, 3rd, Abedin M, Schurmans S, et al. Phosphoinositides Regulate Ciliary Protein Trafficking to Modulate Hedgehog Signaling. *Dev Cell.* 2015; 34(4):400-9.

23. Garcia-Gonzalo F R, and Reiter J F. Scoring a backstage pass: mechanisms of ciliogenesis and ciliary access. *J Cell Biol.* 2012; 197(6):697-709.

24. Raleigh D R, Sever N, Choksi P K, Sigg M A, Hines K M, Thompson B M, et al. Cilia-Associated Oxysterols Activate Smoothened. *Mol Cell.* 2018; 72(2):316-27 e5.

25. Rosenbaum J L, and Witman G B. Intraflagellar transport. *Nature Rev.* 2002; 3(11):813-25.

26. Sarkisian M R, Siebzehnrubl D, Hoang-Minh L, Deleyrolle L, Silver D J, Siebzehnrubl F A, et al. Detection of primary cilia in human glioblastoma. *J. Neurooncol.* 2014; 117(1):15-24.

27. Cai S, Bodle J C, Mathieu P S, Amos A, Hamouda M, Bernacki S, et al. Primary cilia are sensors of electrical field stimulation to induce osteogenesis of human adipose-derived stem cells. *FASEB J.* 2017; 31(1):346-55.

28. Chen Y, Aspera-Werz R H, Menger M M, Falldorf K, Ronniger M, Stacke C, et al. Exposure to 16 Hz Pulsed Electromagnetic Fields Protect the Structural Integrity of Primary Cilia and Associated TGF-beta Signaling in Osteoprogenitor Cells Harmed by Cigarette Smoke. *Intl Mol Sci.* 2021; 22(13).

29. Hoang-Minh L, Deleyrolle L, Nakamura N, Parker A, Martuscello R, Reynolds B, et al. PCM1 depletion inhibits glioblastoma cell ciliogenesis and increases cell death and sensitivity to temozolomide. *Transl Oncol.* 2016; 9 (5): 392-402.

30. Shireman J M, Atashi F, Lee G, Ali E S, Saathoff M R, Park C H, et al. De novo purine biosynthesis is a major driver of chemoresistance in glioblastoma. *Brain.* 2021.

31. Hoang-Minh L B, Dutra-Clarke M, Breunig J J, and Sarkisian M R. Glioma cell proliferation is enhanced in the presence of tumor-derived cilia vesicles. *Cilia.* 2018; 7:6.

32. Shi P, Hoang-Minh L B, Tian J, Cheng A, Basrai R, Kalaria N, et al. HDAC6 Signaling at Primary Cilia Promotes Proliferation and Restricts Differentiation of Glioma Cells. *Cancers (Basel).* 2021; 13(7).

33. Hoang-Minh L B, Deleyrolle L P, Siebzehnrubl D, Ugartemendia G, Futch H, Griffith B, et al. Disruption of KIF3A in patient-derived glioblastoma cells: effects on ciliogenesis, hedgehog sensitivity, and tumorigenesis. *Oncotarget* 2016; 7:7029-43.

34. Linder B, Schiesl A, Voss M, Rodel F, Hehlgans 5, Gullulu O, et al. Dexamethasone Treatment Limits Efficacy of Radiation, but Does Not Interfere With Glioma Cell Death Induced by Tumor Treating Fields. *Front Oncol.* 2021; 11:715031.

35. Romio L, Fry A M, Winyard P J, Malcolm 5, Woolf A S, and Feather S A. OFD1 is a centrosomal/basal body protein expressed during mesenchymal-epithelial transition in human nephrogenesis. *J Am Soc Nephrol.* 2004; 15(10):2556-68.

36. Singla V, Romaguera-Ros M, Garcia-Verdugo J M, and Reiter J F. Ofd1, a human disease gene, regulates the length and distal structure of centrioles. *Dev Cell.* 2010; 18(3):410-24.

37. Tang Z, Lin M G, Stowe T R, Chen S, Zhu M, Stearns T, et al. Autophagy promotes primary ciliogenesis by removing OFD1 from centriolar satellites. *Nature.* 2014; 502(7470):254-7.

38. Qiu H, Fujisawa S, Nozaki S, Katoh Y, and Nakayama K. Interaction of INPPSE with ARL13B is essential for its ciliary membrane retention but dispensable for its ciliary entry. *Biol Open.* 2021; 10(1).

39. Arellano J I, Guadiana S M, Breunig J J, Rakic P, and Sarkisian M R. Development and distribution of neuronal cilia in mouse neocortex. *J Comp Neuro.* 2012; 520(4): 848-73.

40. Berbari N F, Bishop G A, Askwith C C, Lewis J S, and Mykytyn K. Hippocampal neurons possess primary cilia in culture. *J Neurosci Res.* 2007; 85(5):1095-100.

41. Bishop G A, Berbari N F, Lewis J, and Mykytyn K. Type III adenylyl cyclase localizes to primary cilia throughout the adult mouse brain. *J Comp Neurol.* 2007; 505(5):562-71.

42. Guadiana S M, Semple-Rowland S L, Daroszewski D, Madorsky I, Breunig J J, Mykytyn K, et al. Arborization of dendrites by developing neocortical neurons is dependent on primary cilia and type 3 adenylyl cyclase. *J. Neurosci.* 2013; 33:2626-38.

43. Parker A K, Le M M, Smith T S, Hoang-Minh L B, Atkinson E W, Ugartemendia G, et al. Neonatal seizures induced by pentylenetetrazol or kainic acid disrupt primary cilia growth on developing mouse cortical neurons. *Exp Neural.* 2016; 282:119-27.

44. Wang L, and Dynlacht B D. The regulation of cilium assembly and disassembly in development and disease. *Development.* 2018; 145(18).

45. Praetorius H A, and Spring K R. Bending the MDCK cell primary cilium increases intracellular calcium. *J Membr Biol.* 2001; 184(1):71-9.

46. Peixoto E, Jin S, Thelen K, Biswas A, Richard S, Morleo M, et al. HDAC6-dependent ciliophagy is involved in ciliary loss and cholangiocarcinoma growth in human cells and murine models. *Am J Physiol Gastrointest Liver Physiol.* 2020; 318(6):G1022-G33.

47. Akhshi T, and Trimble W S. A non-canonical Hedgehog pathway initiates ciliogenesis and autophagy. *J. Cell Biol.* 2021; 220(1).

48. Pampliega O, Orhon I, Patel B, Sridhar 5, Diaz-Carretero A, Beau I, et al. Functional interaction between autophagy and ciliogenesis. *Nature.* 2014; 502(7470):194-200.

49. Hashimoto M, Tanaka H, Oguro K, and Masuzawa T. Subependymoma of the lateral ventricle-case report. *Neural Med Chir (Tokyo).* 1991; 31(11):732-5.

50. Das R M, and Storey K G. Apical abscission alters cell polarity and dismantles the primary cilium during neurogenesis. Science (New York, NY. 2014; 343(6167):200-4.

51. Mirvis M, Siemers K A, Nelson W J, and Stearns T P. Primary cilium loss in mammalian cells occurs predominantly by whole-cilium shedding. *PLoS Biol.* 2019; 17(7): e3000381.

52. Wang S, Livingston M J, Su Y, and Dong Z. Reciprocal regulation of cilia and autophagy via the MTOR and proteasome pathways. *Autophagy.* 2015; 11(4):607-16.

53. Lam H C, Cloonan S M, Bhashyam A R, Haspel J A, Singh A, Sathirapongsasuti J F, et al. Histone deacetylase 6-mediated selective autophagy regulates COPD-associated cilia dysfunction. *J. Clin Invest.* 2014; 123(12):5212-30.

54. Ishii S, Sasaki T, Mohammad S, Hwang H, Tomy E, Somaa F, et al. Primary cilia safeguard cortical neurons in neonatal mouse forebrain from environmental stress-induced dendritic degeneration. *Proc Natl Acad Sci USA.* 2021; 118(1).

55. Yoshimura K, Kawate T, and Takeda S. Signaling through the primary cilium affects glial cell survival under a stressed environment. *Glia.* 2011; 59(2):333-44.
56. Wurstle S, Schneider F, Ringel F, Gempt J, Lammer F, Delbridge C, et al. Temozolomide induces autophagy in primary and established glioblastoma cells in an EGFR independent manner. *Oncol Lett.* 2017; 14(1):322-8.
57. Yan Y, Xu Z, Dai S, Qian L, Sun L, and Gong Z. Targeting autophagy to sensitive glioma to temozolomide treatment. *J Exp Clin Cancer Res.* 2016; 35:23.
58. Moser J J, Fritzler M J, and Rattner J B. Primary ciliogenesis defects are associated with human astrocytoma/glioblastoma cells. *BMC Cancer.* 2009; 9:448.
59. Moser J J, Fritzler M J, and Rattner 1B. Ultrastructural characterization of primary cilia in pathologically characterized human glioblastoma multiforme (GBM) tumors. *BMC Clin Pathol.* 2014; 14:40.
60. Zhao X, Pak E, Ornell K I, Pazyra-Murphy M F, MacKenzie E L, Chadwick E J, et al. A Transposon Screen Identifies Loss of Primary Cilia as a Mechanism of Resistance to SMO Inhibitors. *Cancer Discov.* 2017; 7(12):1436-49.
61. Deleyrolle L P, Harding A, Cato K, Siebzehnrubl F A, Rahman M, Azari H, et al. Evidence for label-retaining tumour-initiating cells in human glioblastoma. *Brain.* 2011; 134(Pt 5):1331-43.
62. Hothi P, Martins T J, Chen L, Deleyrolle L, Yoon J G, Reynolds B, et al. High-throughput chemical screens identify disulfiram as an inhibitor of human glioblastoma stem cells. *Oncotarget* 2012; 3(10):1124-36.
63. Lin B, Lee H, Yoon J G, Madan A, Wayner E, Tonning S, et al. Global analysis of H3K4me3 and H3K27me3 profiles in glioblastoma stem cells and identification of SLC17A7 as a bivalent tumor suppressor gene. *Oncotarget* 2015; 6(7):5369-81.

We claim:

1. A method of determining susceptibility of cancer cells of a subject to treatment with alternating electric fields, the method comprising:

applying alternating electric fields to a first batch of cancer cells obtained or derived from a subject;

after applying the alternating electric fields to the first batch of cancer cells ascertaining via imaging or RT-PCR or by determining a level of ARG13B or OTD1 a first percentage of the cancer cells of the first batch that are ciliated;

ascertaining a second percentage of a second batch of cancer cells obtained or derived from the subject that are ciliated, wherein the second batch of cancer cells was not exposed to alternating electric fields prior to ascertaining the second percentage, wherein the first percentage of ciliated cancer cells is lower than the second percentage of ciliated cancer cells; and after ascertaining the first and second percentages of cancer cells that are ciliated, treating cancer cells of in the subject with alternating electric fields.

2. The method of claim 1, the first percentage of ciliated cancer cells is at least 20% lower than the second percentage of ciliated cancer cells.

3. The method of claim 1, wherein a frequency of the alternating electric fields is between 50 kHz and 1 MHz.

4. The method of claim 1, wherein a frequency of the alternating electric fields is 200 kHz.

5. The method of claim 1, wherein the percentages of the cancer cells that are ciliated are ascertained by imaging cancer cells.

6. The method of claim 5, wherein the imaging is performed by confocal microscopy or light microscopy.

7. The method of claim 1, wherein the percentages of the cancer cells that are ciliated are ascertained by RT-PCR.

8. The method of claim 1, wherein the percentages of the cancer cells that are ciliated are ascertained by determining a level of ARL13B in the first batch and the second batch.

9. The method of claim 1, wherein the percentages of the cancer cells that are ciliated are ascertained by determining a level of OTD1 in the first batch and the second batch.

10. A method of reducing the viability of cancer cells of a subject, comprising:

applying alternating electric fields to a first batch of cancer cells obtained or derived from a subject;

ascertaining, after applying the alternating electric fields to the first batch of cancer cells, a first percentage of the cancer cells of the first batch that are ciliated;

ascertaining a second percentage of a second batch of cancer cells obtained or derived from the subject that are ciliated, wherein the second batch of cancer cells was not exposed to alternating electric fields prior to ascertaining the second percentage, wherein the first percentage of ciliated cancer cells is lower than the second percentage of ciliated cancer cells; and after ascertaining the first and second percentages of cancer cells that are ciliated, applying alternating electric fields to the subject.

11. The method of claim 10, wherein the first percentage of ciliated cancer cells is at least 20% lower than the second percentage of ciliated cancer cells.

12. The method of claim 10, wherein a frequency of the alternating electric fields is between 50 kHz and 1 MHz.

13. The method of claim 10, wherein a frequency of the alternating electric fields is 200 kHz.

14. The method of claim 10, wherein the alternating electric fields are applied for at least 12 hours.

15. The method of claim 10, wherein the alternating electric fields are applied for at least 24 hours.

16. The method of claim 10, wherein the alternating electric fields are applied for at least 72 hours.

17. The method of claim 10, further comprising administering a chemotherapeutic agent to the cancer cells.

18. The method of claim 17, wherein the chemotherapeutic agent is TMZ.

19. The method of claim 17, wherein the chemotherapeutic agent is a checkpoint inhibitor.

* * * * *